(12) United States Patent
Kornerup et al.

(10) Patent No.: US 7,648,494 B2
(45) Date of Patent: Jan. 19, 2010

(54) INFUSION SET AND INJECTOR DEVICE FOR INFUSION SET

(75) Inventors: Grete Kornerup, Vipperød (DK); Lasse Wesseltoft Mogensen, Søborg (DK); Magnus Walter Göransson, Malmö (SE)

(73) Assignee: Unomedical A/S, Birkeroed (DK)

( * ) Notice: Subject to any disclaimer, the term of this patent is extended or adjusted under 35 U.S.C. 154(b) by 359 days.

(21) Appl. No.: 11/084,893

(22) Filed: Mar. 21, 2005

(65) Prior Publication Data
US 2005/0215979 A1    Sep. 29, 2005

Related U.S. Application Data

(60) Provisional application No. 60/556,863, filed on Mar. 26, 2004.

(30) Foreign Application Priority Data
Mar. 26, 2004  (DK) ............................... 2004 00493

(51) Int. Cl.
*A61M 25/16* (2006.01)
(52) U.S. Cl. ............. 604/539; 604/164.01; 604/164.04; 604/164.07; 604/164.12; 604/165.03; 604/174; 604/272
(58) Field of Classification Search ................... 604/19, 604/21, 48, 502, 506, 93.01, 164.01, 164.04, 604/164.07, 164.11–164.12, 165.01, 165.03, 604/170.01, 170.02, 174, 175, 179, 181, 604/200, 201, 264, 272, 890.1, 539, 70.01; 600/564, 566–567
See application file for complete search history.

(56) References Cited

U.S. PATENT DOCUMENTS

| | | | |
|---|---|---|---|
| 643,544 A | 2/1900 | Simmons |
| 1,838,825 A | 12/1931 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 5/1954 | Lindblad |
| 2,730,099 A | 1/1956 | Sullivan |
| 2,839,060 A | 6/1958 | Ormo |

(Continued)

FOREIGN PATENT DOCUMENTS

DE        893 296        12/1953

(Continued)

*Primary Examiner*—Nicholas D Lucchesi
*Assistant Examiner*—Quynh-Nhu H Vu
(74) *Attorney, Agent, or Firm*—Brinks Hofer Gilson & Lione

(57) ABSTRACT

An infusion set having an infusion part for insertion into a patient and a connector for connecting the infusion part with a medical device through a tube is provided. The connector is axially displaceable relative to the infusion part. The infusion part includes an adhesive support, a base part with a first set of guiding means and at least two retention devices for locking the connector to the infusion part, a cannula extending from the base part and being in fluid communication with a cavity. The cavity is further adapted to receive a second cannula extending from the connector where the second cannula is in fluid communication with the tube. The infusion set further includes a second set of guiding means that are adapted to fit with the first set of guiding means and at least two arms. The retention devices extend from an upper surface of a main surface of the base part and the arms include means corresponding to the retention members.

27 Claims, 34 Drawing Sheets

U.S. PATENT DOCUMENTS

| | | |
|---|---|---|
| 2,936,141 A | 5/1960 | Rapata |
| 2,952,420 A | 9/1960 | Von Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,317,166 A | 5/1967 | Janssen |
| 3,545,286 A | 12/1970 | Stenstrom |
| 3,547,119 A | 12/1970 | Hall et al. |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,942,528 A | 3/1976 | Loeser |
| 3,986,508 A | 10/1976 | Barrington |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,267,836 A | 5/1981 | Whitney et al. |
| 4,306,705 A | 12/1981 | Svenson |
| 4,315,505 A | 2/1982 | Crandall et al. |
| 4,334,551 A | 6/1982 | Pfister |
| D267,199 S | 12/1982 | Koenig |
| 4,365,630 A | 12/1982 | McFlarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,473,369 A | 9/1984 | Lueders et al. |
| 4,500,312 A | 2/1985 | McFarlane |
| 4,517,971 A | 5/1985 | Sorbonned |
| 4,530,695 A | 7/1985 | Phillips et al. |
| 4,531,686 A | 7/1985 | Shaw |
| 4,531,937 A | 7/1985 | Yates |
| 4,563,177 A | 1/1986 | Kamen |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,129,884 A | 7/1992 | Dysarz |
| 5,134,593 A | 7/1992 | Logan et al. |
| 5,134,594 A | 7/1992 | Woo |
| 5,137,516 A | 8/1992 | Rand et al. |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,650 A | 1/1993 | Haining |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| 5,439,473 A * | 8/1995 | Jorgensen .................. 606/182 |
| D362,718 S | 9/1995 | Deily et al. |
| 5,449,349 A | 9/1995 | Sallee et al. |
| 5,451,210 A | 9/1995 | Kramer et al. |
| 5,487,506 A | 1/1996 | Drummond et al. |
| 5,490,841 A | 2/1996 | Landis |

| Patent | Kind | Date | Inventor | Ref |
|---|---|---|---|---|
| 5,492,313 | A | 2/1996 | Pan et al. | |
| 5,505,709 | A | 4/1996 | Funderburk et al. | |
| 5,507,730 | A | 4/1996 | Haber et al. | |
| 5,519,167 | A | 5/1996 | Kunimoto et al. | |
| 5,520,654 | A | 5/1996 | Wahlberg | |
| 5,522,803 | A | 6/1996 | Teisson-Simony | |
| 5,527,287 | A * | 6/1996 | Miskinyar | 604/135 |
| 5,533,974 | A | 7/1996 | Gaba | |
| 5,540,709 | A | 7/1996 | Ramel | |
| 5,545,143 | A | 8/1996 | Fischell | |
| 5,545,152 | A | 8/1996 | Funderburk et al. | |
| 5,554,130 | A | 9/1996 | McDonald et al. | |
| 5,558,650 | A | 9/1996 | McPhee | |
| 5,562,636 | A | 10/1996 | Utterberg | |
| 5,575,777 | A | 11/1996 | Cover et al. | |
| 5,584,813 | A | 12/1996 | Livingston et al. | |
| 5,591,188 | A | 1/1997 | Waisman | |
| 5,599,309 | A | 2/1997 | Marshall et al. | |
| 5,599,315 | A | 2/1997 | McPhee | |
| 5,599,318 | A | 2/1997 | Sweeney et al. | |
| 5,628,765 | A * | 5/1997 | Morita | 606/182 |
| 5,643,214 | A | 7/1997 | Marshall et al. | |
| 5,643,216 | A | 7/1997 | White | |
| 5,643,220 | A | 7/1997 | Cosme | |
| 5,662,617 | A | 9/1997 | Odell et al. | |
| 5,665,071 | A | 9/1997 | Wyrick | |
| 5,665,075 | A | 9/1997 | Gyure et al. | |
| 5,676,156 | A | 10/1997 | Yoon | |
| 5,681,323 | A | 10/1997 | Arick | |
| 5,695,476 | A | 12/1997 | Harris | |
| 5,704,920 | A | 1/1998 | Gyure | |
| 5,709,516 | A | 1/1998 | Peterson et al. | |
| 5,714,225 | A | 2/1998 | Hansen et al. | |
| 5,738,641 | A | 4/1998 | Watson et al. | |
| 5,741,288 | A | 4/1998 | Rife | |
| 5,752,923 | A | 5/1998 | Terwilliger | |
| 5,810,835 | A | 9/1998 | Ryan et al. | |
| 5,817,058 | A | 10/1998 | Shaw | |
| 5,820,598 | A | 10/1998 | Gazza et al. | |
| 5,833,666 | A | 11/1998 | Davis et al. | |
| D402,538 | S | 12/1998 | Wagter et al. | |
| 5,843,001 | A | 12/1998 | Goldenberg | |
| 5,848,990 | A | 12/1998 | Cirelli et al. | |
| 5,851,197 | A | 12/1998 | Marano et al. | |
| 5,858,001 | A | 1/1999 | Tsals et al. | |
| 5,865,806 | A | 2/1999 | Howell | |
| 5,873,540 | A | 2/1999 | Hardin | |
| 5,899,886 | A | 5/1999 | Cosme | |
| 5,913,846 | A | 6/1999 | Szabo | |
| 5,915,640 | A | 6/1999 | Wagter et al. | |
| 5,919,167 | A | 7/1999 | Mulhauser et al. | |
| 5,925,032 | A | 7/1999 | Clements | |
| 5,947,931 | A | 9/1999 | Bierman | |
| 5,947,935 | A | 9/1999 | Rinehart et al. | |
| 5,951,523 | A | 9/1999 | Osterlind et al. | |
| 5,954,643 | A * | 9/1999 | VanAntwerp et al. | 600/316 |
| 5,957,892 | A | 9/1999 | Thorne | |
| 5,968,011 | A | 10/1999 | Larsen et al. | |
| 5,975,120 | A | 11/1999 | Novosel | |
| 5,980,488 | A | 11/1999 | Thorne | |
| 5,980,506 | A * | 11/1999 | Mathiasen | 604/535 |
| 5,984,224 | A | 11/1999 | Yang | |
| 5,984,897 | A | 11/1999 | Petersen et al. | |
| 5,992,787 | A | 11/1999 | Burke | |
| D417,733 | S | 12/1999 | Howell et al. | |
| 6,017,328 | A | 1/2000 | Fischell et al. | |
| D421,119 | S | 2/2000 | Musgrave et al. | |
| 6,039,629 | A | 3/2000 | Mitchell | |
| 6,042,570 | A | 3/2000 | Bell et al. | |
| 6,045,533 | A | 4/2000 | Kriesel et al. | |
| 6,050,976 | A | 4/2000 | Thorne et al. | |
| 6,056,718 | A | 5/2000 | Funderburk et al. | |
| 6,056,726 | A | 5/2000 | Isaacson | |
| 6,074,371 | A | 6/2000 | Fischell | |
| 6,077,244 | A | 6/2000 | Botich et al. | |
| 6,086,008 | A | 7/2000 | Gray et al. | |
| 6,086,575 | A | 7/2000 | Mejslov | |
| 6,090,068 | A | 7/2000 | Chanut | |
| 6,093,172 | A | 7/2000 | Funderburk et al. | |
| 6,093,179 | A | 7/2000 | O'Hara et al. | |
| 6,099,503 | A | 8/2000 | Stardella | |
| 6,105,218 | A | 8/2000 | Reekie | |
| 6,120,482 | A | 9/2000 | Szabo | |
| 6,123,690 | A | 9/2000 | Mejslov | |
| 6,132,755 | A | 10/2000 | Eicher et al. | |
| 6,159,181 | A | 12/2000 | Crossman et al. | |
| 6,183,464 | B1 | 2/2001 | Sharp et al. | |
| 6,191,338 | B1 | 2/2001 | Haller | |
| 6,193,694 | B1 | 2/2001 | Bell et al. | |
| 6,219,574 | B1 | 4/2001 | Cormier et al. | |
| 6,221,058 | B1 | 4/2001 | Kao et al. | |
| 6,248,093 | B1 | 6/2001 | Moberg | |
| 6,293,925 | B1 | 9/2001 | Safabash et al. | |
| 6,302,866 | B1 | 10/2001 | Marggi | |
| 6,319,232 | B1 | 11/2001 | Kashmer | |
| 6,322,535 | B1 | 11/2001 | Hitchins et al. | |
| 6,322,808 | B1 | 11/2001 | Trautman et al. | |
| 6,334,856 | B1 | 1/2002 | Allen et al. | |
| 6,355,021 | B1 | 3/2002 | Nielsen et al. | |
| 6,379,335 | B1 | 4/2002 | Rigon et al. | |
| D456,692 | S | 5/2002 | Epstein | |
| 6,387,076 | B1 | 5/2002 | Van Landuyt | |
| 6,450,992 | B1 | 9/2002 | Cassidy, Jr. | |
| 6,488,663 | B1 * | 12/2002 | Steg | 604/164.08 |
| 6,517,517 | B1 | 2/2003 | Farrugia et al. | |
| 6,520,938 | B1 * | 2/2003 | Funderburk et al. | 604/164.08 |
| D472,316 | S | 3/2003 | Douglas et al. | |
| D472,630 | S | 4/2003 | Douglas et al. | |
| 6,572,586 | B1 * | 6/2003 | Wojcik | 604/165.01 |
| 6,579,267 | B2 | 6/2003 | Lynch et al. | |
| 6,582,397 | B2 | 6/2003 | Alesi et al. | |
| 6,595,962 | B1 | 7/2003 | Perthu | |
| 6,607,509 | B2 | 8/2003 | Bobroff et al. | |
| 6,607,511 | B2 | 8/2003 | Halseth et al. | |
| 6,620,136 | B1 | 9/2003 | Pressly, Sr. et al. | |
| 6,629,949 | B1 | 10/2003 | Douglas | |
| 6,645,182 | B1 | 11/2003 | Szabo | |
| 6,685,674 | B2 | 2/2004 | Douglas et al. | |
| 6,702,779 | B2 | 3/2004 | Connelly et al. | |
| 6,726,649 | B2 | 4/2004 | Swenson et al. | |
| 6,736,797 | B1 | 5/2004 | Larsen et al. | |
| 6,749,589 | B1 | 6/2004 | Douglas et al. | |
| 6,790,199 | B1 | 9/2004 | Gianakos | |
| 6,805,686 | B1 | 10/2004 | Fathallah et al. | |
| 6,811,545 | B2 | 11/2004 | Vaillancourt | |
| 6,814,720 | B2 | 11/2004 | Olsen et al. | |
| 6,824,530 | B2 | 11/2004 | Wagner et al. | |
| 6,824,531 | B1 | 11/2004 | Zecha, Jr. et al. | |
| 6,830,562 | B2 | 12/2004 | Mogensen et al. | |
| 6,837,877 | B2 | 1/2005 | Zurcher | |
| 6,840,922 | B2 | 1/2005 | Nielsen et al. | |
| 6,880,701 | B2 | 4/2005 | Bergeron et al. | |
| 6,916,017 | B2 | 7/2005 | Noe | |
| 6,923,791 | B2 | 8/2005 | Douglas | |
| 6,926,694 | B2 | 8/2005 | Marano-Ford et al. | |
| 6,939,331 | B2 | 9/2005 | Ohshima | |
| 6,949,084 | B2 | 9/2005 | Marggi et al. | |
| 6,979,316 | B1 * | 12/2005 | Rubin et al. | 604/156 |
| 7,018,344 | B2 | 3/2006 | Bressler et al. | |
| 7,056,302 | B2 | 6/2006 | Douglas | |
| 7,214,207 | B2 * | 5/2007 | Lynch et al. | 604/93.01 |
| 7,303,543 | B1 * | 12/2007 | Maule et al. | 604/93.01 |
| 2001/0004970 | A1 | 6/2001 | Hollister et al. | |
| 2001/0016714 | A1 | 8/2001 | Bell et al. | |
| 2001/0021827 | A1 | 9/2001 | Ferguson et al. | |
| 2001/0039401 | A1 | 11/2001 | Ferguson et al. | |

| | | |
|---|---|---|
| 2001/0041875 A1 | 11/2001 | Higuchi et al. |
| 2002/0022855 A1 | 2/2002 | Bobroff et al. |
| 2002/0068904 A1 | 6/2002 | Pluth et al. |
| 2002/0072720 A1 | 6/2002 | Hague et al. |
| 2002/0077599 A1 | 6/2002 | Wojcik |
| 2002/0107489 A1 | 8/2002 | Lee |
| 2002/0111581 A1 | 8/2002 | Sasso |
| 2002/0145073 A1 | 10/2002 | Swanson |
| 2002/0156424 A1 | 10/2002 | Suzuki et al. |
| 2002/0156427 A1 | 10/2002 | Suzuki et al. |
| 2002/0161332 A1* | 10/2002 | Ramey .................. 604/164.07 |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1* | 3/2003 | Mogensen et al. .......... 604/257 |
| 2003/0069548 A1 | 4/2003 | Connelly et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1* | 3/2004 | Lynch et al. .............. 604/93.01 |
| 2004/0049159 A1 | 3/2004 | Barrus et al. |
| 2004/0068231 A1 | 4/2004 | Blondeau |
| 2004/0087913 A1 | 5/2004 | Rogers et al. |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1* | 8/2004 | Hunn et al. ............ 604/164.01 |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0199123 A1 | 10/2004 | Nielsen |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0043687 A1 | 2/2005 | Mogensen et al. |
| 2005/0075606 A1 | 4/2005 | Botich et al. |
| 2005/0101910 A1 | 5/2005 | Bowman et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119637 A1 | 6/2005 | Lundgren et al. |
| 2005/0124936 A1 | 6/2005 | Mogensen et al. |
| 2005/0159709 A1 | 7/2005 | Wilkinson |
| 2005/0215979 A1 | 9/2005 | Kornerup et al. |
| 2005/0251098 A1 | 11/2005 | Wyss et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0030815 A1 | 2/2006 | Csincsura et al. |
| 2006/0041224 A1 | 2/2006 | Jensen |
| 2006/0173413 A1 | 8/2006 | Fan |

FOREIGN PATENT DOCUMENTS

| | | |
|---|---|---|
| DE | 1 053 541 | 3/1959 |
| DE | 26 20 009 A1 | 12/1977 |
| DE | 28 03 509 | 8/1979 |
| DE | 28 03 509 A | 8/1979 |
| DE | 37 15 965 A | 1/1988 |
| DE | 196 31 921 | 3/1997 |
| DE | 298 18 311 U1 | 3/1999 |
| DE | 299 05 072 U1 | 9/1999 |
| DE | 298 18 311 U1 | 11/1999 |
| DE | 19847143 A1 | 1/2000 |
| DE | 101 06 074 A1 | 9/2000 |
| DE | 299 21 406 | 1/2001 |
| DE | 101 06 074 A1 | 6/2002 |
| DE | 299 21 406 U1 | 11/2002 |
| DK | 37 22 893 C1 | 6/1988 |
| DK | 38 23 447 | 2/1996 |
| DK | 196 10 692 A1 | 9/1997 |
| DK | 198 47 143 A1 | 1/2000 |
| DK | 100 49 001 A1 | 4/2002 |
| EP | 0 188 014 B1 | 10/1985 |
| EP | 0 239 244 B1 | 2/1987 |
| EP | 0 290 176 A1 | 11/1988 |
| EP | 0 298 521 B1 | 9/1990 |
| EP | 0 451 040 A1 | 10/1991 |
| EP | 0 184 231 B1 | 1/1992 |
| EP | 0 475 857 | 3/1992 |
| EP | 0 544 837 B1 | 6/1993 |
| EP | 0 633 039 | 7/1994 |
| EP | 0 651 662 B1 | 5/1995 |
| EP | 0 714 631 B1 | 6/1996 |
| EP | 744 183 A2 | 11/1996 |
| EP | 0 747 006 A1 | 12/1996 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0 956 879 A1 | 11/1999 |
| EP | 0 615 768 A2 | 12/1999 |
| EP | 1 045 145 A1 | 10/2000 |
| EP | 1 060 757 A1 | 12/2000 |
| EP | 1 086 718 A | 3/2001 |
| EP | 1 125 593 A1 | 8/2001 |
| EP | 1 167 765 A2 | 1/2002 |
| EP | 0 775 501 | 6/2002 |
| EP | 0 894 216 B1 | 7/2003 |
| EP | 1 329 233 A1 | 7/2003 |
| EP | 1 380 315 A1 | 1/2004 |
| EP | 0 956 879 A1 | 7/2004 |
| FR | 576 849 | 8/1924 |
| FR | 576849 | 8/1924 |
| FR | 2 611 013 | 8/1988 |
| FR | 2725902 | 10/1994 |

| | | |
|---|---|---|
| FR | 2 733 915 | 11/1996 |
| FR | 2733915 A1 | 11/1996 |
| FR | 2 781 617 A1 | 1/2000 |
| FR | 2781617 A1 | 1/2000 |
| GB | 478803 | 1/1938 |
| GB | 591730 | 3/1946 |
| GB | 906574 | 9/1962 |
| GB | 1 268 575 | 3/1972 |
| GB | 1 403 034 | 8/1975 |
| GB | 2 224 808 A | 5/1990 |
| GB | 2 270 552 A | 3/1994 |
| JP | 5326062 A | 12/1993 |
| JP | 05326062 A | 12/1993 |
| JP | 7051251 | 11/1995 |
| JP | 9217584 A | 9/1997 |
| JP | 2000-59877 A | 2/2000 |
| JP | 3140740 | 2/2000 |
| JP | 2000059877 A | 2/2000 |
| JP | 3140740 B2 | 3/2001 |
| JP | 2002-028246 | 1/2002 |
| NL | 1017427 C | 11/2002 |
| WO | WO 87/06474 | 11/1987 |
| WO | WO 93/03787 | 3/1993 |
| WO | WO 93/05840 | 4/1993 |
| WO | WO 94/20160 | 9/1994 |
| WO | WO 95/28327 A | 10/1995 |
| WO | WO 96/32981 A1 | 10/1996 |
| WO | WO 96/35472 A1 | 11/1996 |
| WO | WO 98/09065 | 3/1998 |
| WO | WO 98/58693 | 12/1998 |
| WO | WO 99/07435 | 2/1999 |
| WO | WO 99/33504 | 7/1999 |
| WO | WO 99/36009 | 7/1999 |
| WO | WO 99/56802 | 11/1999 |
| WO | WO 99/61815 | 12/1999 |
| WO | WO 00/02614 | 1/2000 |
| WO | WO 00/03757 | 1/2000 |
| WO | WO 00/44324 A1 | 8/2000 |
| WO | WO 01/04507 A1 | 1/2001 |
| WO | WO 01/30419 A2 | 5/2001 |
| WO | WO 01/68180 | 9/2001 |
| WO | WO 01/81785 A1 | 11/2001 |
| WO | WO 01/93926 A2 | 12/2001 |
| WO | WO 02/46080 | 6/2002 |
| WO | WO 02/066854 A1 | 8/2002 |
| WO | WO 02/081012 A2 | 10/2002 |
| WO | WO 02/094352 | 11/2002 |
| WO | WO 02/100457 | 12/2002 |
| WO | WO 02/102442 A1 | 12/2002 |
| WO | WO 02/068014 | 1/2003 |
| WO | WO 03/015860 A1 | 2/2003 |
| WO | WO 03/026728 | 4/2003 |
| WO | WO 2004/030726 A | 4/2004 |
| WO | WO 2004/087240 | 10/2004 |
| WO | WO 2005/004973 | 1/2005 |

* cited by examiner

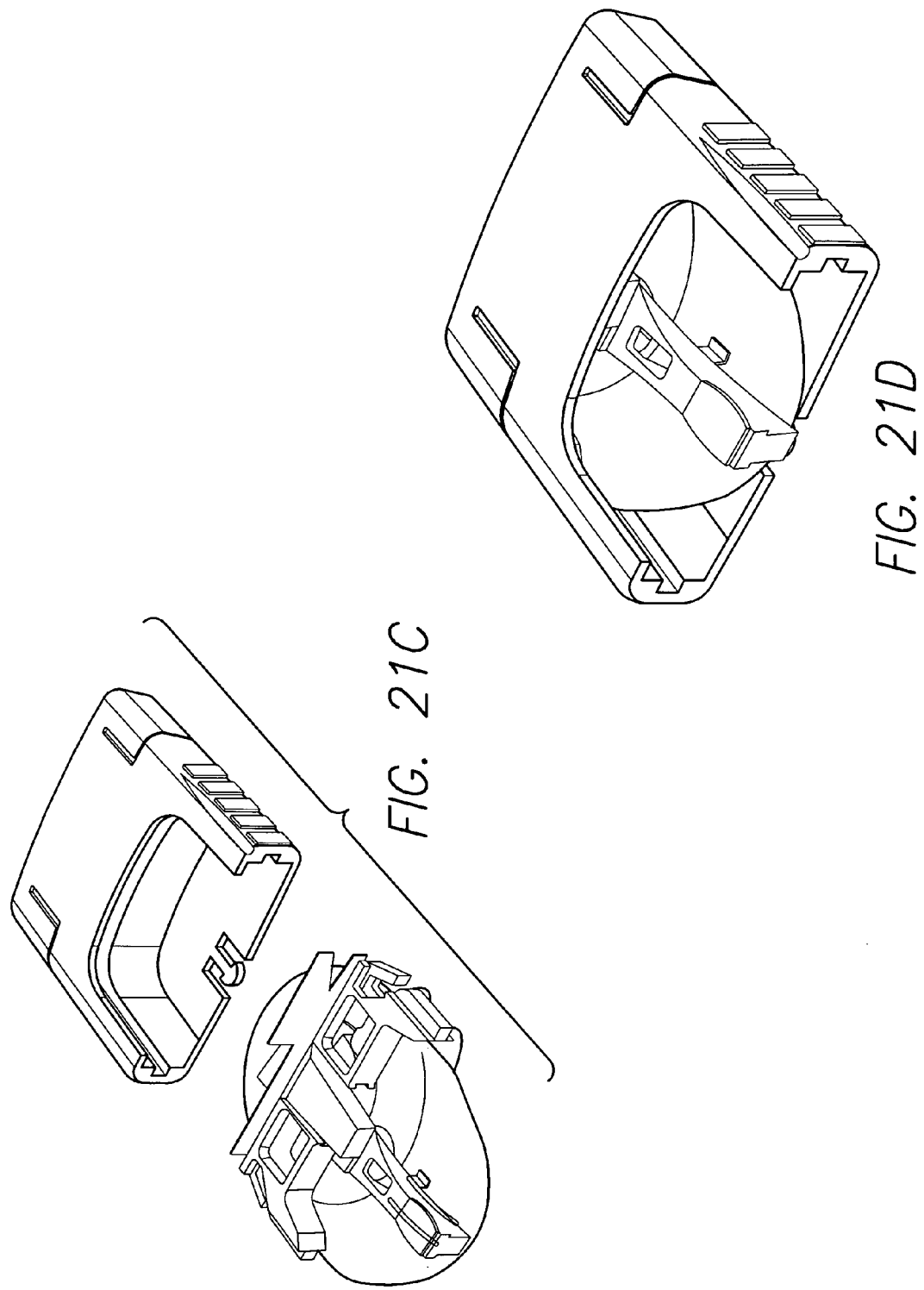

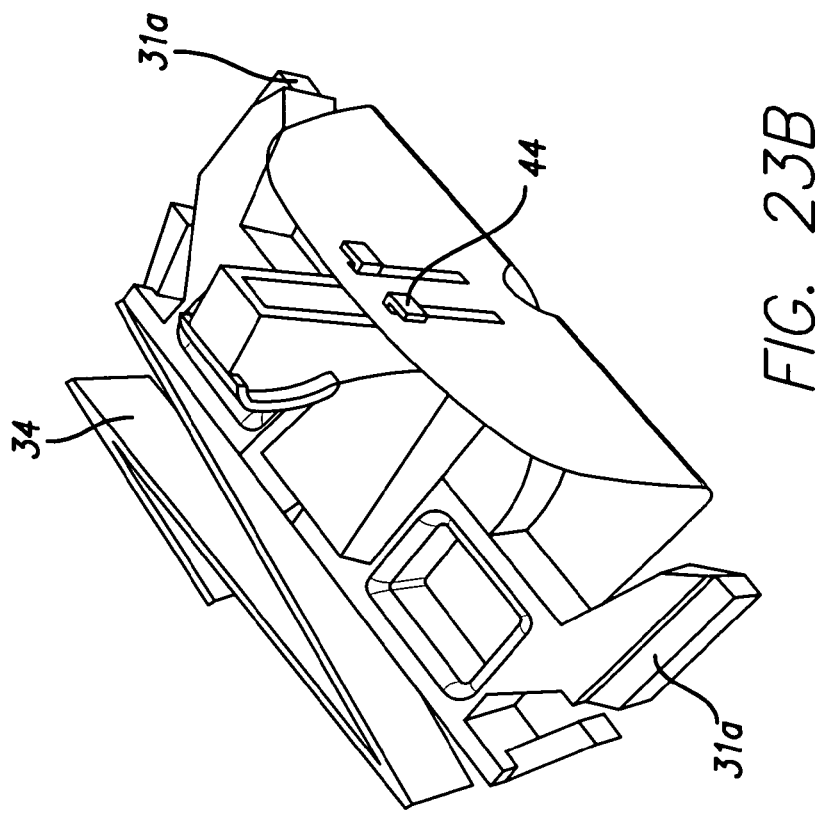
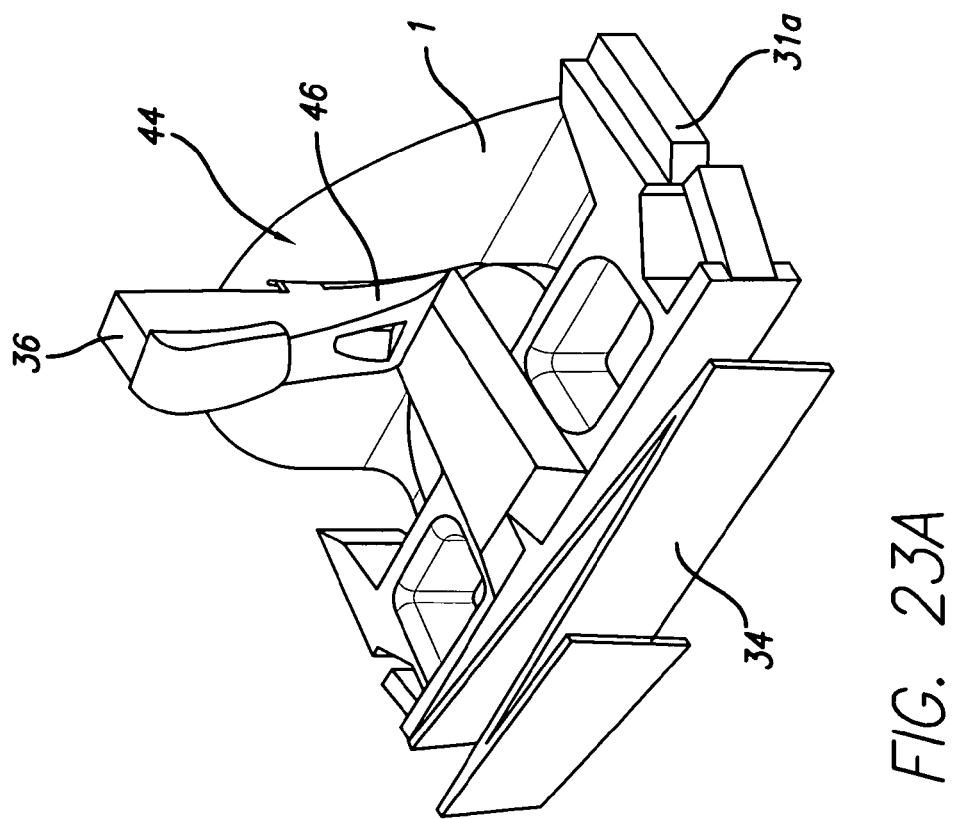
FIG. 23A
FIG. 23B

US 7,648,494 B2

INFUSION SET AND INJECTOR DEVICE FOR INFUSION SET

This application claims priority to Danish Patent Application No. PA 200400493, filed Mar. 26, 2004 and U.S. Provisional Application No. 60/556,863, filed Mar. 26, 2004.

TECHNICAL FIELD

The invention relates to an infusion set for an intermittent or continuous administration of a therapeutical substance, such as insulin and an injector device for an infusion set. An infusion set comprises an infusion part with a cannula to penetrate the skin of a person and a connector for connecting the infusion part with a medical device preferably a medical delivery device such as an insulin pump.

An infusion set has in its assembled form a substantially planar rear side and a relatively large width compared to its thickness, thus allowing it to lie flat on the patient's skin and thereby minimizing the discomfort of carrying the infusion set.

The infusion part is placed in the patient for a longer and not specified time period while the connector is supposed to be connected and disconnected from time to time. Hereby it is possible for the patient to disconnect from the medical device, move around and at a later point re-connect to the medical device. Further it is possible to shift between different medical devices using the same infusion part and thereby there is only need for one penetration of the skin which provides less discomfort to the patient.

The injector device according to the present invention is especially directed towards situations where patients wants to or has to insert the infusion part by themselves without the assistance of educated personnel.

BACKGROUND

U.S. Pat. No. 5,522,803 discloses an infusion set having an infusion part and a connector. The infusion part comprises a soft plastic cannula in liquid communication with a cavity for receiving a needle from a connector, two sloping guiding holes and two retention devices; and the connector comprises a cannula, two square guiding pins and two arms with a hooking part for gripping the retention device of the infusion part and operating in the main plane of the infusion part.

A lot of patients e.g. insulin patients have to or may desire to insert an infusion device or to place a subcutaneous sensor or the like themselves. For some persons it is a troublesome process to perform the skin penetration themselves, they therefore need a device which assists them in this process and thereby making the process less problematic.

U.S. Pat. No. 6,572,586B1 discloses an infusion set for administration of a fluid to a subcutaneous layer and include a cannula housing adapted for mounting onto a patient's skin and a needle housing for connection to the cannula housing. The needle housing has a pair of flexible sidewalls and a resilient band connected to the sidewalls. The resilient band is lockably engage able with the cannula housing thereby securing the housings together, and the resilient band is releasable from the cannula housing when pressing the sidewalls toward each other to deform the resilient band. A hollow needle extends out of a main body of the needle housing for delivering fluid to the cannula from a fluid source. The walls of the needle housing extend beyond a distal end of the hollow needle to prevent needle contact with contaminated surfaces an inadvertent injury.

In both of these infusion sets two arms are formed along the sides of the connector part and the movement performed to unrelease the connector from the infusion part is in both cases pressing the two arms together. Compared to these to constructions the present invention is of a more simple form and also the locking mechanism according to the invention allows for the user to actually see when the arms are unlocked, especially if the infusion part and the connector are toned in different colors.

Given that the infusion part is supposed to be connected and especially disconnected several times with the connector it is important that this operation is painless and simple to perform.

The document US 2003/0225373 discloses an insertion device for inserting an infusion part or a sensor into a patient. The device comprises a housing, a coil spring, a safety device and part for angling the insertion into the patient. However the apparatus is relatively complicated to manufacture industrially and further the device has to be loaded manually by the patient by a rather complicated procedure.

WO 03/026728 A1 discloses an injector device comprising a housing, a spring, a slidable bar, a locking mechanism and a needle.

SUMMARY OF THE INVENTION

The object of the invention is to provide an infusion set with a coupling mechanism which can be connected and separated with as less discomfort to the patient as possible, and which infusion set is also easy for the patient to find out and to operate.

It is also an object of the invention to provide an improved insertion device which is easy to manufacture and which is suitable for being delivered in a loaded form or at least being easier to load. Especially elderly people, who can have some motor problems, need an insertion device which exists in a pre-loaded form.

According to the invention there is provided an infusion set comprising an infusion part for insertion into a patient and a connector for connecting the infusion part with a medical device through a tube. The connector is axially displaceable relative to the infusion part, said infusion part comprising an adhesive support, a base part with a first set of guiding means and at least two retention devices for locking the connector to the infusion part, a cannula extending from said base part and being in fluid communication with a cavity which is optionally covered with a membrane, said cavity being further adapted to receive a second cannula extending from the connector, which second cannula is in fluid communication with the tube, a second set of guiding means adapted to fit with the first set of guiding means and at least two arms where the retention devices are extending from the upper surface of the main surface of the base part and the arms comprise means corresponding to the retention means.

The above described infusion set is easier to disconnect and will seem safer to use for the patient than previously known infusion sets. All that is needed to separate the connector from the infusion part is a slight simultaneous pressure on the two arms of the connector and the user will be able to see how the connection/disconnection between the infusion part and the connector takes place.

With the term cavity is meant the inner lumen of the cannula or the extension of the cannula.

In a preferred embodiment the connector is symmetrical both around the main plain of the connector and around the plane being perpendicular to the main plane and being parallel to the central axis, thus allowing the connector to be connected to the infusion part no matter which of the main sides is facing upwards. This results in an easier operation of the infusion set.

The arms of the connector can appropriately be provided with gripping means for getting a better grip of the connector. Examples of such gripping means could be but are not limited to rims, grooves, recesses, and a roughened surface optionally of another material than the connector itself, preferably recesses are used. This results in a safer and more comforting operation of the infusion set since the risk that the fingers slip during handling resulting in unintended movements of the infusion part and the cannula is reduced.

In one embodiment of the invention the connector has a reduced material content e.g. in the form of at least one groove, preferably at least two grooves, placed where the arms are connected to the central part of the connector comprising the second set of guiding means (8), thus allowing the arms of the connector to move perpendicular to the base part while the second set of guiding means are stationary. This makes it possible to disconnect the connector from the infusion part by lifting the arms instead of pressing them towards each other. Hereby it is achieved that connection/disconnection can be performed in a manner which at the same time reduces the stresses in the material during the operation, eases the operation of the locking mechanism and reduces the patient's unpleasantness during the connection/release of the connector.

In another embodiment retention devices are positioned on a particularly flexible part of the base part. The flexible part can be provided by choosing an appropriate material for the base part or by providing very thin parts of material between the retention parts and the center of the base part, but preferably the base part of the infusion part has at least two cuttings forming at least two flaps. The formed flexible parts are able to in an elastic manner to move out of the main plane of the infusion part. Hereby the same advantages during connection/release as described above are obtained.

In a preferred embodiment the cannula of the infusion part penetrates the adhesive support, thus stabilizing the position of the infusion part relative to the point of skin penetration to an even greater extend. Further this minimizes the risk that the cannula is accidently withdrawn from the patient.

In a preferred embodiment the adhesive support is a plaster.

In a preferred embodiment the infusion part and the connector are made from two different plastics materials, such as two different types of polypropylene.

In a preferred embodiment there is a visual difference in the toning of the connector and the base part of the infusion part. Hereby it is achieved that it is easier for the patient to see the separation line between the two units resulting in an easier operation of the locking mechanism.

In a preferred embodiment the retention devices are in form of at least two steps placed on either the infusion part or the connector and a matching carving in the other part. Preferably the step has a side with a triangular shape thus forming the step as a sloping hill. Preferably the retention devices are placed on the infusion part and the matching carvings are placed in the connector's arms.

In a preferred embodiment the tube is a flexible plastics material which preferably is connected with the rest of the connector by means of glue.

Preferably the medical delivery device is a drug delivery device such as an insulin delivery device e.g. in the form of an insulin pump.

The cannula of the connector can be a hard cannula, preferably a metal cannula such as a steel cannula. Also the cannula of the connector can be made of a plastics material and/or being blunt.

In a preferred embodiment the cannula is a soft cannula preferably a soft cannula made of a plastics material. Preferred plastics materials for the soft cannula are materials which are sufficiently flexible to bend, when the patient moves and sufficiently rigid to avoid kinking, closing off the drug supply. Further the material must be compatible with medical use i.e. irritation of the skin must be kept at a minimum, being non-toxic it must not decompose in the body, etc. Thermoplastic elastomers (TPE) are a type of material which fulfils these requirements. Examples of such useful elastomers are: polyester ethers, ECDEL, styrene based TPE, olefin based TPE, urethane based TPE, ester based TPE, amid based TPE, polyolefins and silicone rubbers. In a preferred embodiment the material is selected from the group consisting of polypropylene, C-FLEX™, mixtures of C-FLEX™ and polypropylene, LUPOLEN™ 1840H, LUPOLEN™ 3020D, PELLETHANE™ 2363-75D, PELLETHANE™ 2363-55D, TECOTHANE™ and CARBOTHANE™.

In a preferred embodiment the infusion part and the connector are made of polypropylene.

Given that the infusion part is supposed to be connected and especially disconnected several times with the connector it is important that the cannula of the connector is guided safely into the cavity of the infusion part and that the cannula in the disconnected situation is protected as much as possible. It is therefore a further object of the invention to provide an infusion set with an improved guiding mechanism and with an improved protection of the connector cannula.

In a preferred embodiment the connector cannula is extending from the central part of the connector and being placed in a withdrawn position relative to the front of the central part and at least one of the first set of guiding means comprises at least two stabilizing fins.

The above described invention provides an infusion set with an improved protection of the cannula of the connector thus allowing the connector to be connected and disconnected from the infusion part more times than in the previously known infusion sets.

A lot of patients e.g. insulin patients have to or may desire to insert an infusion device or to place a subcutaneous sensor or the like themselves. For some persons it is a troublesome process to perform the skin penetration themselves, they therefore need a device which assists them in this process thereby making the process less problematic.

The advantage in essentially vertical insertion is that it is easier to control the dept of the needle penetration and thereby the dept of the cannula. This is important in self-insertion of the infusion part.

According to the invention an injector device is provided for the subcutaneous introduction of a cannula of an infusion part into the skin of a patient. The injector device comprises a housing, a back and longitudinally extending guiding means, a member which is longitudinally slidable within the housing, an insertion needle for insertion in the cavity of said cannula, a spring located between the back of the housing and the longitudinally slidable member, locking means for maintaining the spring in a compressed state and release means for disengaging the locking means characterized in that the device further comprises a pivoting member which can be swung from a position in which the pivoting member allows for insertion of the needle into a position in which the pivoting member embraces the needle.

The insertion device according to this invention is easy to handle in a safe way before, during and after use, even if the user has reduced dexterity in the hands. Also the user can choose an essentially vertical insertion which makes it easier to control the dept of the needle penetration and thereby the insertion dept of the cannula. This is important in self-insertion of the infusion part. Besides the injector is of a very simple construction which makes it possible to reduce costs of production.

The insertion needle can during insertion be unreleasably attached to the slidable member, unreleasably attached to the infusion part thereby being the cannula or the insertion needle can be a separate unit which the user removes after insertion.

In a preferred embodiment the pivoting member is fastened to the slidable member. This makes production of the unit simpler, and also the pivoting member will need to be shorter than if the pivoting member was fastened to the housing. If the pivoting member is fastened to the slidable member, the position where the pivoting member allows for insertion of the needle is preferably in an angle v where v≈45° or larger in order for the pivoting member to be bend backwards when touching the user, preferably v≈90° or larger in order for the pivoting member not to hit the user during insertion. The angle v is the angle between the central axis of the injection device which is parallel to the insertion needle, and the pivoting member.

In a preferred embodiment the insertion device has means for temporarily fixing the pivoting member in an essentially right angle relative to the housing thus stabilizing the insertion device in an essentially vertical position relative to the skin to be penetrated prior to penetration. This is particularly relevant for patients with motor problems since they can have problems to control the insertion angle.

Preferably the housing has means for getting a better grip of the injector device. Examples of such means could be but are not limited to rims, grooves, recesses, a roughened surface optionally of another material than the housing itself, preferably recesses are used There will be different possibilities for placing the pivoting member in the position where it embraces the needle but in a preferred embodiment the pivoting member embraces the needle when the slidable member is in a forward position and the spring is in a released state. Often when using injection devices in connection with insertion of infusion sets the user is supposed to bring the insertion needle back into the housing in order to protect the surroundings from the used insertion needle. This means the users has to work against the spring force, which was pushing the needle forward during insertion, and at the same time the user has to avoid the used needle, when bringing it back into the housing. This can be quite difficult for a user which might have reduced dexterity of the hands and fingers. According to the present invention it will be quite easy for the user to secure the insertion needle as turning the relatively large pivoting member does not call for the use of strength.

In one embodiment the insertion needle is destroyed and secured as the pivoting member is placed in a final position embracing the needle. This will make it safe to dispose of the used insertion device with ordinary garbage.

In one embodiment the pivoting arms are also the locking means and it has a tab functioning as disengaging means.

In another embodiment there is separate locking means and disengaging means. Preferably the pivoting member then still have a tab for securing the arm in a position parallel to the axis of the housing until it is desired to swing the pivoting member to the position in which it embraces the needle.

Preferably the pivoting member embraces the needle in a first position being parallel to the main axis of the injector device then it is swung into a second position being essentially orthogonal to said main axis and then finally swung into a position in which it embraces the needle.

In a preferred embodiment the pivoting member is swung from the position essentially orthogonal to said main axis, 180 degrees to another position embracing the needle and being secured in this position said position also being essentially orthogonal to the main axis. Optionally the needle is destroyed in the process and secured in the pivoting member.

In another preferred embodiment the infusion part to be inserted is provided with an adhesive support unreleasably fastened to the infusion part and having an adhesive surface, which adhesive surface is provided with a release liner.

In this embodiment the pivoting member can have fixing means for releasably fastening a part of the adhesive support to the pivoting member. This construction assures that the adhesive support is folded in an appropriate way during insertion, which results in that the adhesive support will turn a part of the adhesive surface towards the user's skin, when the infusion part is inserted.

In another preferred embodiment the release liner of the adhesive support can also have one or more projecting parts. Describing parts as projecting from the release liner means that the parts are not necessarily in contact with the adhesive surface of the adhesive support, the projecting part or parts extend beyond the part of the release liner being in protecting contact with the adhesive surface. One of the projecting parts can be fastened unreleasably to the housing in order to at least partly have the release liner removed from the adhesive support during insertion of the needle. The total removal of the release liner will take place after insertion of the needle when the injector device is taken away for disposal and the release liner will—as it is still attached to the injection device—be removed and disposed off together with the used injector device.

In a more preferred embodiment the release liner comprises at least two separate pieces, and each piece has at least one projecting part. This makes it possible to remove the release liner automatically during insertion without the release liner coming into conflict with the insertion needle.

Preferably the projecting part of the first piece of release liner is attached to the pivoting member during insertion and the projecting part of the second piece of release liner is attached to the housing during insertion. This embodiment makes it easier for the user to remove the release liner during/after insertion and at the same time the adhesive surface of the adhesive support is completely protected before insertion.

In a preferred embodiment of the invention the pivoting member of the injector device further has means for temporarily fixing the adhesive support of the infusion part. Hereby it is achieved that the adhesive support does not fold in an unsuitable manner during insertion of the infusion part.

Preferably the injector device comprises means for stopping the slidable member in its most forward position preferably in form of a stopping tab.

BRIEF DESCRIPTION OF THE DRAWINGS

In the following the invention will be described in further details with reference to the figures.

FIG. 21A-D shows assembling of the infusion part and injector device according to the third embodiment.

FIG. 23A-B shows the adhesive support of the infusion part hooked to the slidable member.

DETAILED DESCRIPTION OF THE INVENTION

Figure 1:
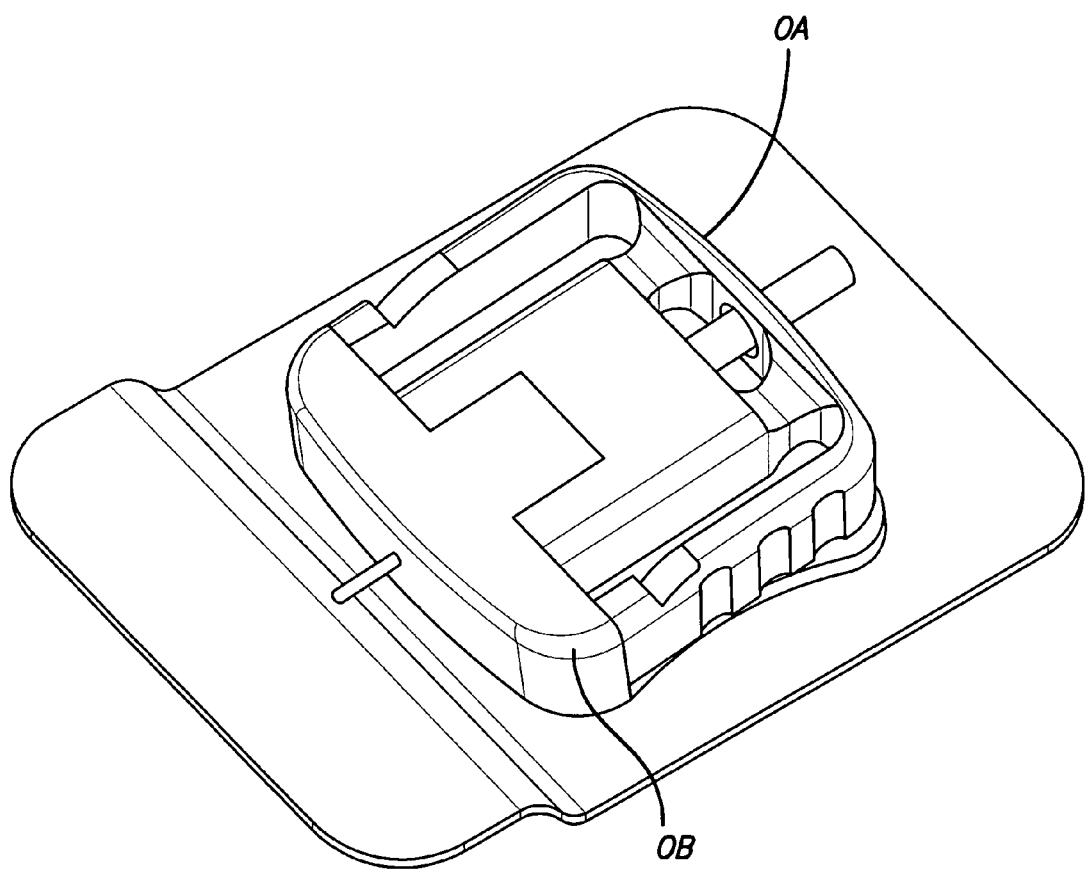
FIG. 1 shows one embodiment of an infusion set where the infusion part and the connector are unified.
Figure 2:
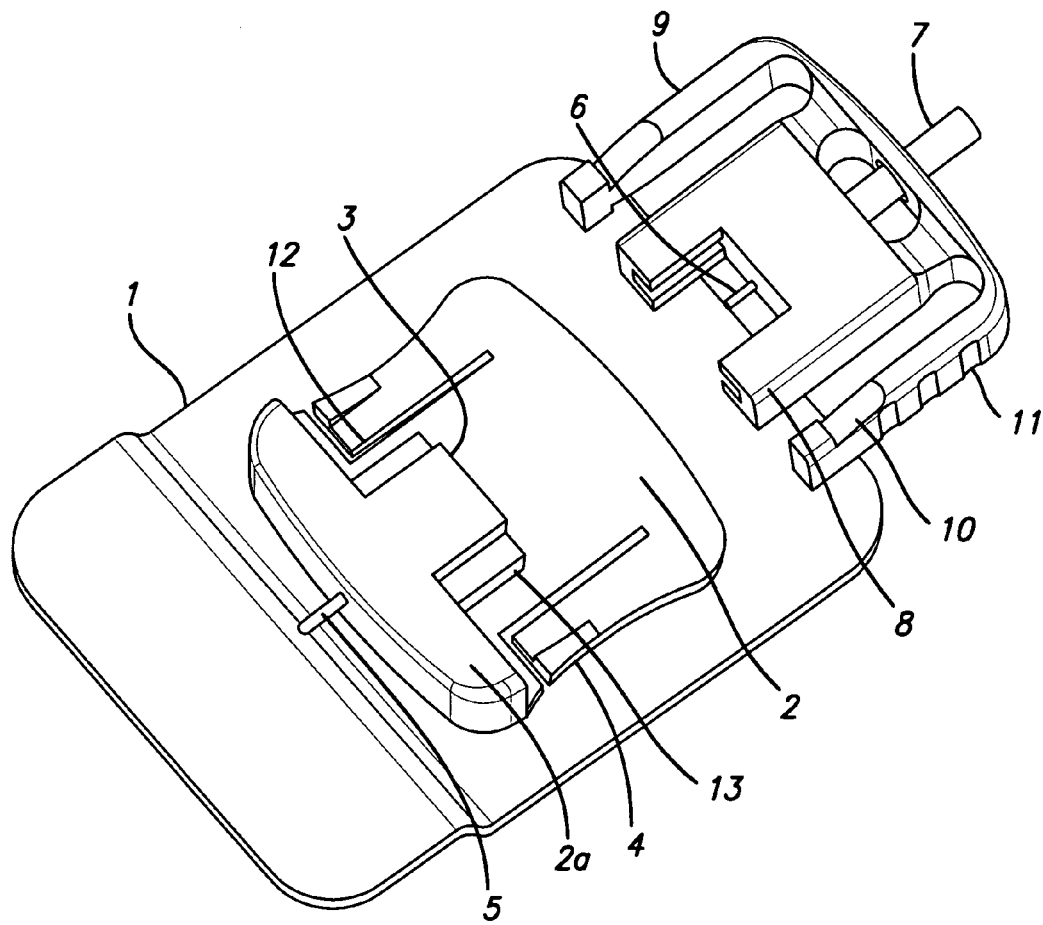
FIG. 2 shows one embodiment of the infusion set where the infusion part and the connector are separated.
Figure 3:
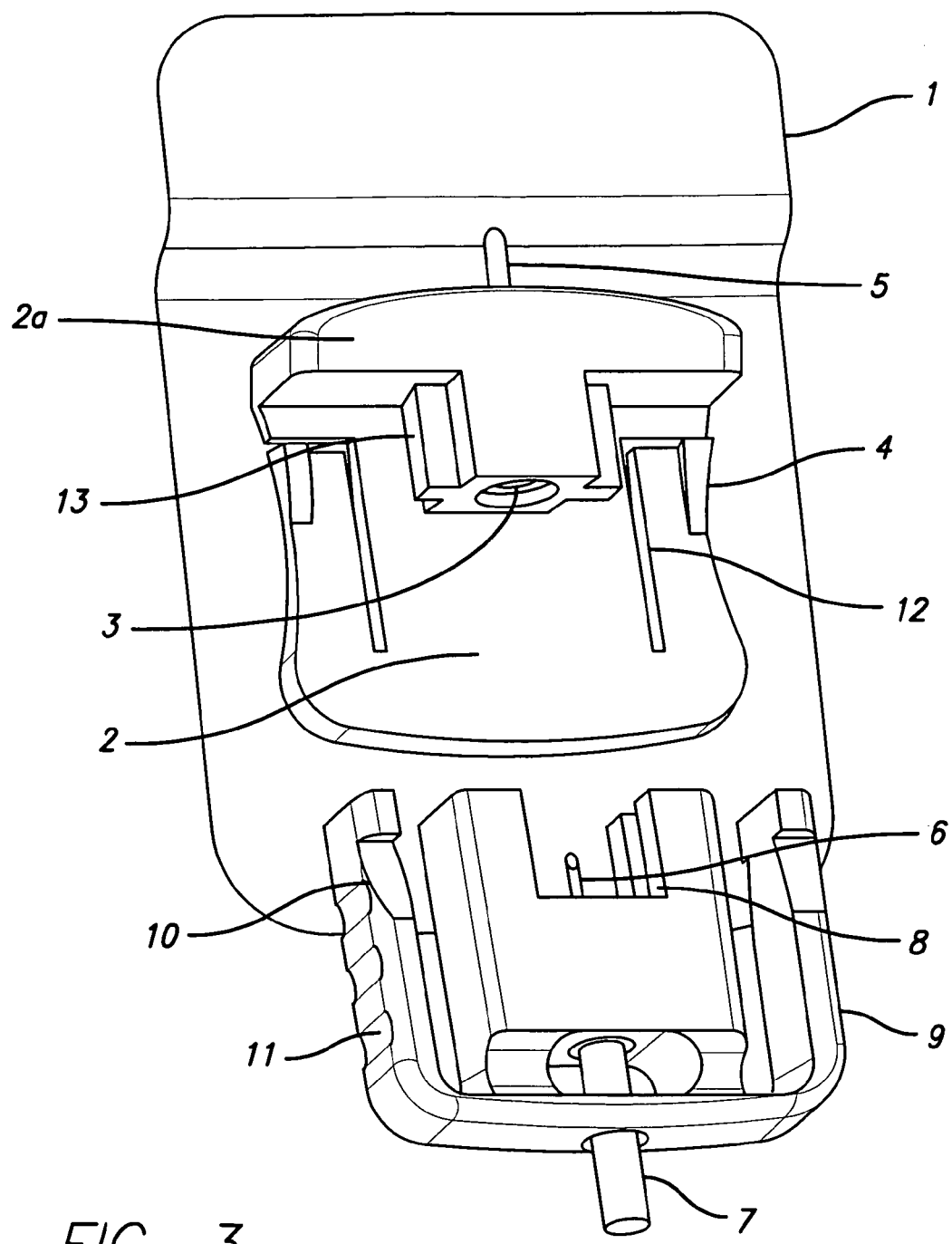
FIG. 3 shows the same embodiment of the separated infusion set as in FIG. 2 from a different angle.
Figure 4:
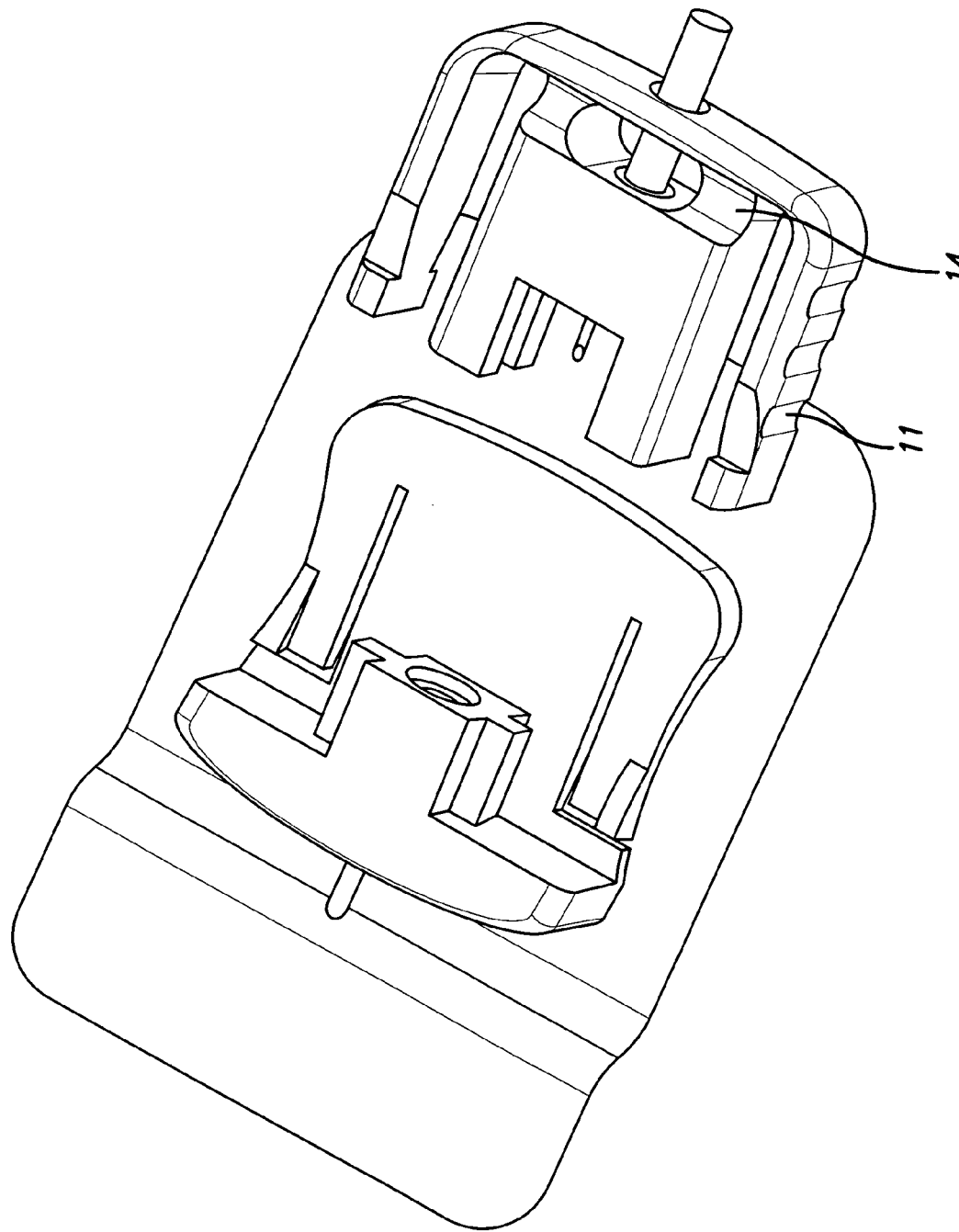
FIG. 4 shows a second embodiment of a separated infusion set from a first angle.
Figure 5:
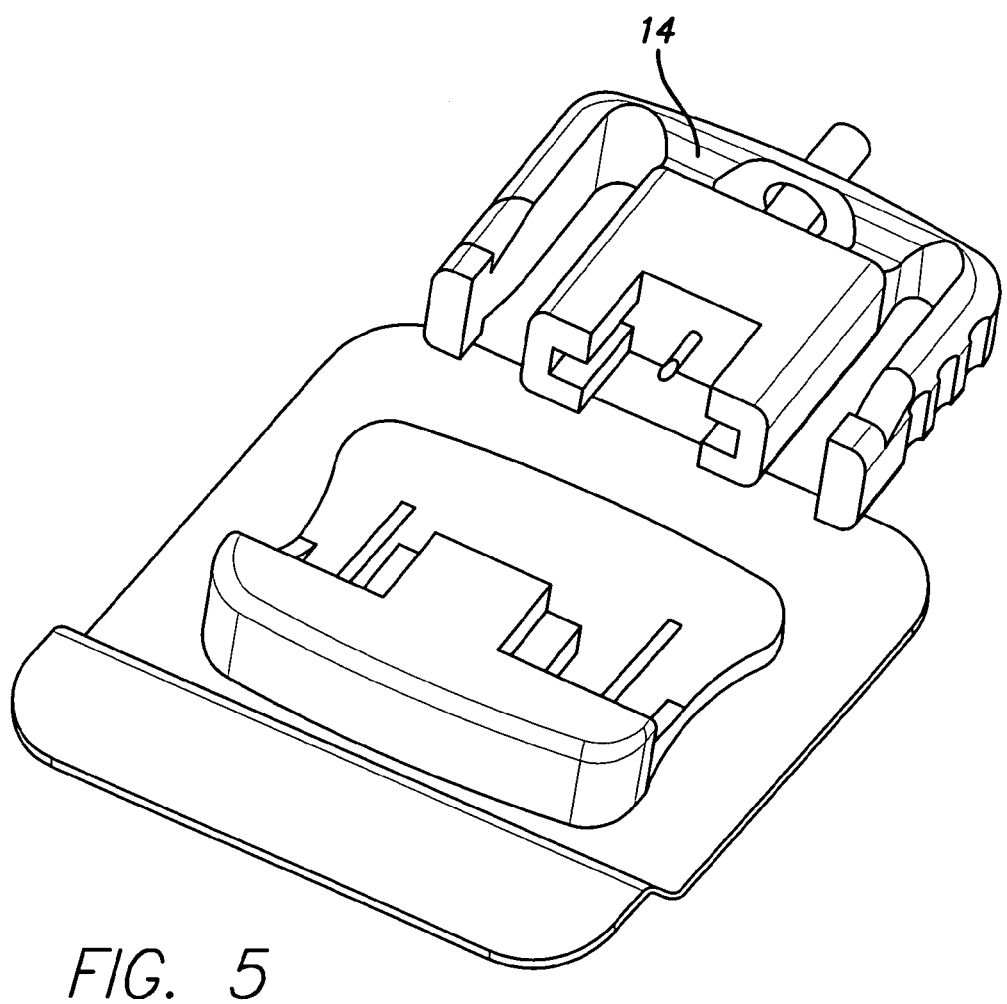
FIG. 5 shows the second embodiment of the infusion set from a different angle.

FIG. 1-3 illustrates an embodiment of an infusion set. The infusion set comprises an infusion part (0B) and a connector (0A). The infusion part (0B) comprises a base part (2) having a main plane which, when the infusion set is attached to a patient, is essentially parallel to the skin of the patient, and a shoulder part (2a) protecting the connector part (0A) from being released unintentionally. Said base part (2) comprises a first set of guiding means (13) which in this case has the form of two stabilizing fins. The base part further comprises two retention devices (4) extending from the upper surface of the base part in this case in form of two steps. Mounted on the inner surface of the infusion part is an adhesive support (1) which in this case is a plaster. A cannula (5) is extending from the base part (2) and is penetrating the adhesive support (1) being in fluid communication with a central cavity (3). The cannula (5) is preferably a soft cannula but could also be made of metal. The cavity (3) optionally being covered by a membrane is adapted to receive a second cannula (6) extending from the connector. In the embodiment shown in FIG. 2-5 the second cannula (6) is extending from the central part of the connector and is placed in a retracted position relative to the front of the central part. In this embodiment the base part (2) has two cuttings (12) creating two flaps on which the retention devices (4) are mounted. The connector (0A) comprises two arms (9) having four carvings (10) adapted to fit with the retention devices (4). The connector (0A) is symmetrical around the main plane and around the plane perpendicular to the main plane and parallel to the main axis thus allowing the connector to match with the base part in two ways. The cannula (6) is in fluid communication with the tube (7) which provides the connection to a medical device such as an insulin pump. In this embodiment the central part of the connector has a second set of guiding means (8) in form of two grooves placed symmetrically around the main plane of the connector. In this embodiment the connector further has gripping means (11) in form of recesses. The gripping means 11 are optional and can be selected from the group consisting of rims, grooves, recesses or a roughened surface optionally of another material than the connector itself FIGS. 4 and 5 show another embodiment of the invention where the connector has two grooves (14) which in this case are placed symmetrically around the main plane of the connector. However it is not necessary for the grooves to be places symmetrically around the main plane since they are not coupling with the infusion part.

Whether the infusion set is intended to be inserted manually or by an injector the infusion part (0B) and the connector (0A) are delivered to the user as two separate units in sterile packages. When inserted manually the infusion part (0B) will at delivery be combined with a needle unit with the same locking and guiding means (8) as the connector. The needle unit is provided with an insertion needle extending from the central front which insertion needle at delivery extends through and beyond the end of the cannula (5). The needle unit's only function will be to penetrate the user's skin where after the needle unit is removed and replaced with the connector (0A) leaving the cannula (5) subcutaneous.

The connector (0A) can be connected to a luer coupling member through the tube (7). Through the luer coupling it is possible to administer a suitable therapeutical substance, such as insulin from a pump. The connector can also be a sort of closing part with a suitable entrance for an inserting needle of a syringe. Such a closing part can stay in position for up till three days while the user can have medication, e.g. insulin injected through the entrance in order to reduce trauma to the skin caused by repeated penetration of the skin.

It is important for the user that it is easy to change i.e. to engage and to disengage the infusion part (0B) and the connector (0A) even when the user has reduced dexterity. The present invention complies with this purpose as the movement used to unlock the infusion part (0B) from the connector (0A) is pressing the connector between the first finger and the thumb which is simple and easily performed movement. Also the oppositely directed forces from respectively the first finger and the thumb pushing toward each other, are not only used to unlock the device but is also used when pulling the connector away from the infusion part (0B). In order to make it easier to disengage the connector (0A) the arms (9) can be made very flexible, either by choosing a soft and flexible material or by making the fastening of the arms (9) to the central part more or less rigid e.g. by varying the size of the grooves (14) on the shoulder of the connector (0A).

Although the arms (9) are very flexible the danger of accidently pulling the connector away from the infusion part when positioned on the skin of the user is quite small as the device has to be exposed to a simultaneous pressure from both sides.

Another advantage of the invention according to the present invention is that only a very small amount of material need to be used when producing the infusion part. The infusion part (0B) can be reduced to:

- a slim central part comprising the cannula (5), the cavity (3) and guiding means (13),
- a shoulder part (2a) connected to the central part and protecting the ends of the movable arms (9) of the connector when the connector is engaged with the infusion part, and
- a base part (2) which has been reduced to two arms connected to the central part which arms are provided with the retention means (4).

Figure 6:
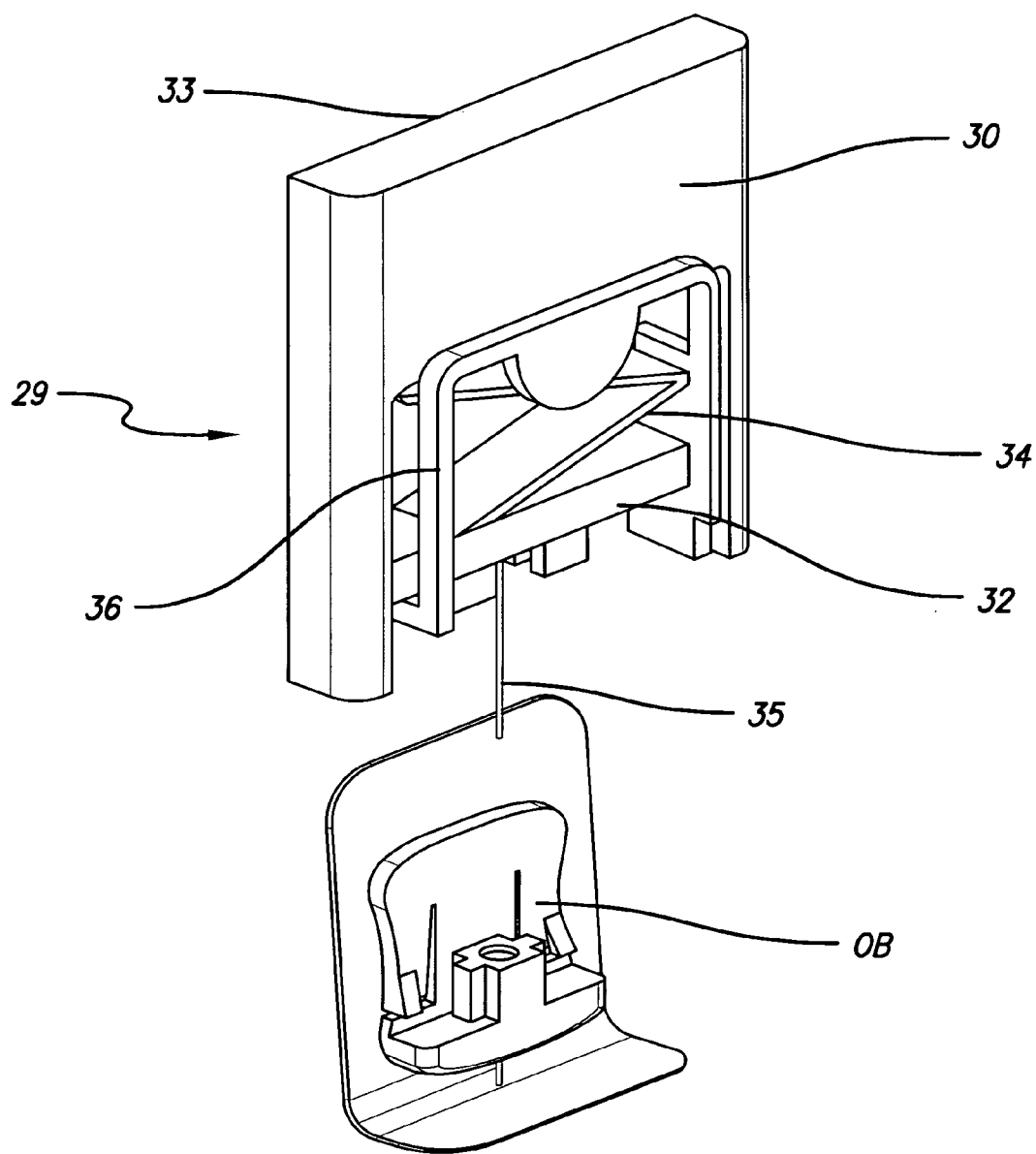
FIG. 6 shows a first embodiment of an injector device separated from the infusion part.
Figure 7:
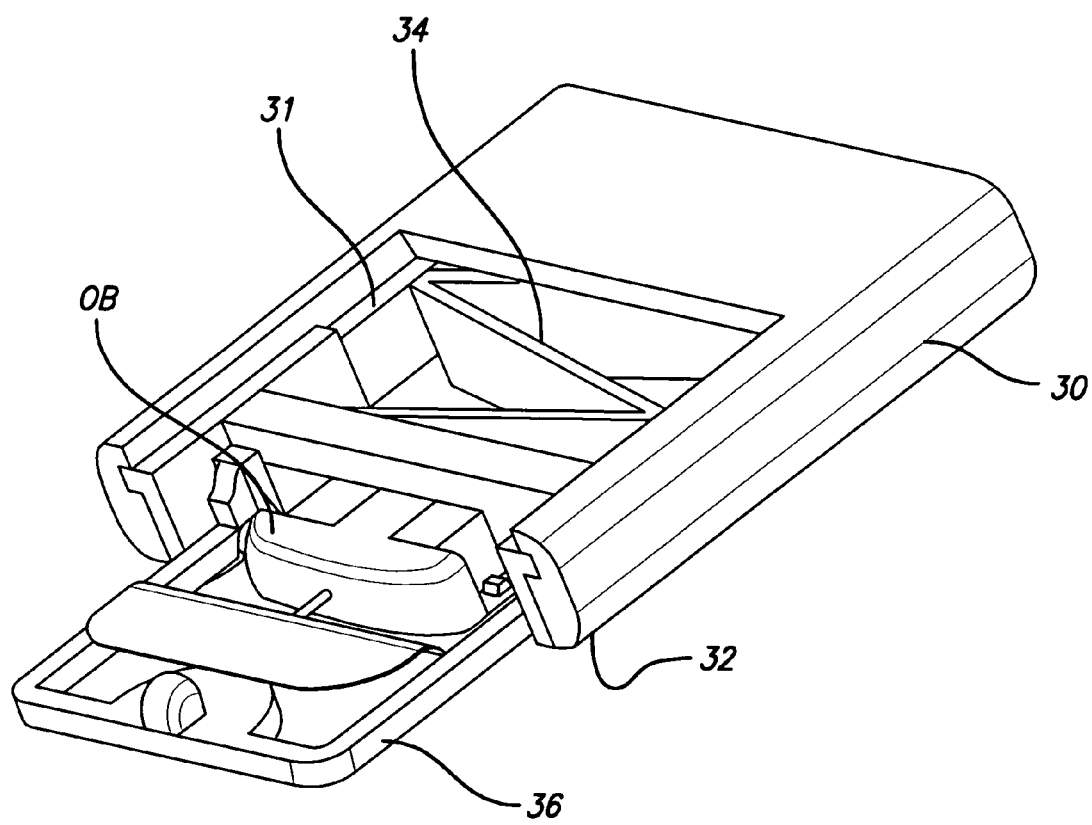
FIG. 7 shows the first embodiment of the injector device joined with the infusion part.
Figure 8:
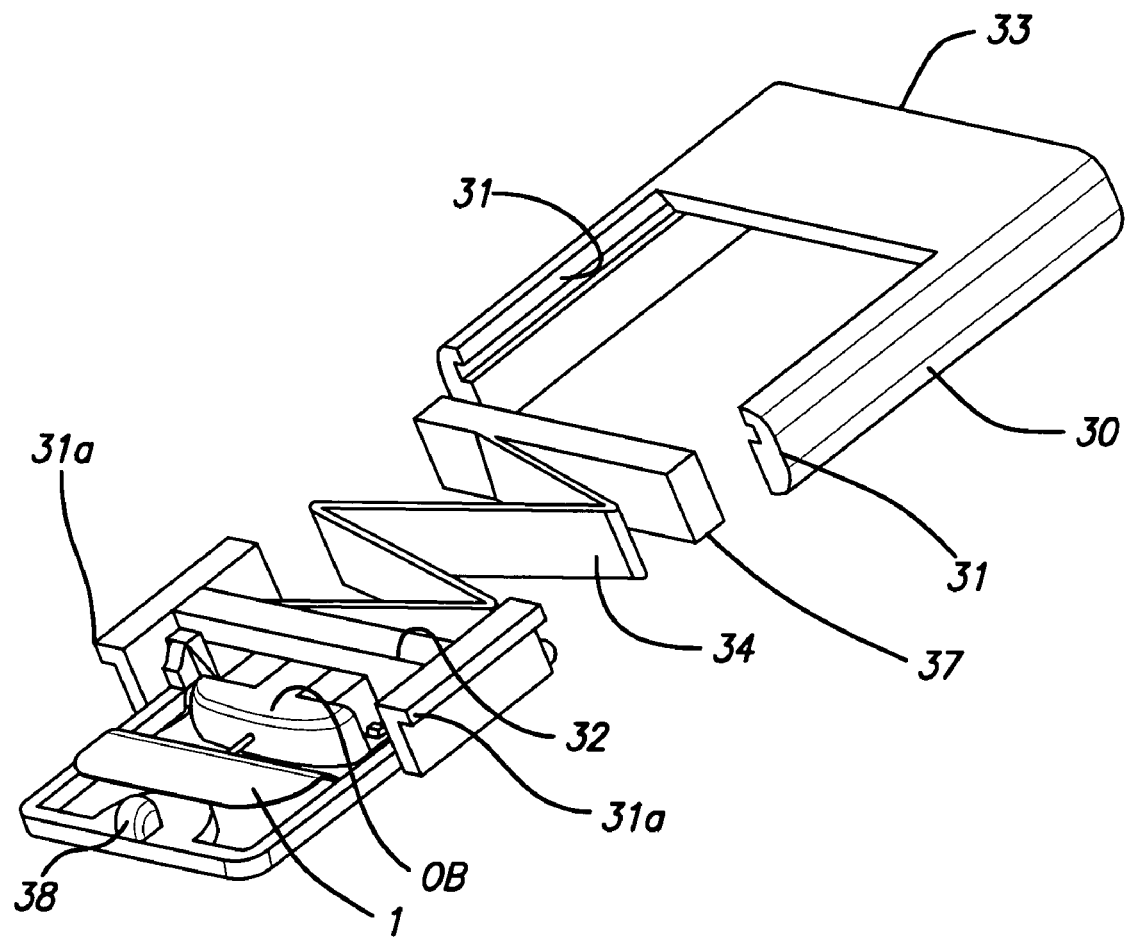
FIG. 8 shows the first embodiment of the injector device joined with the infusion part.
Figure 9:
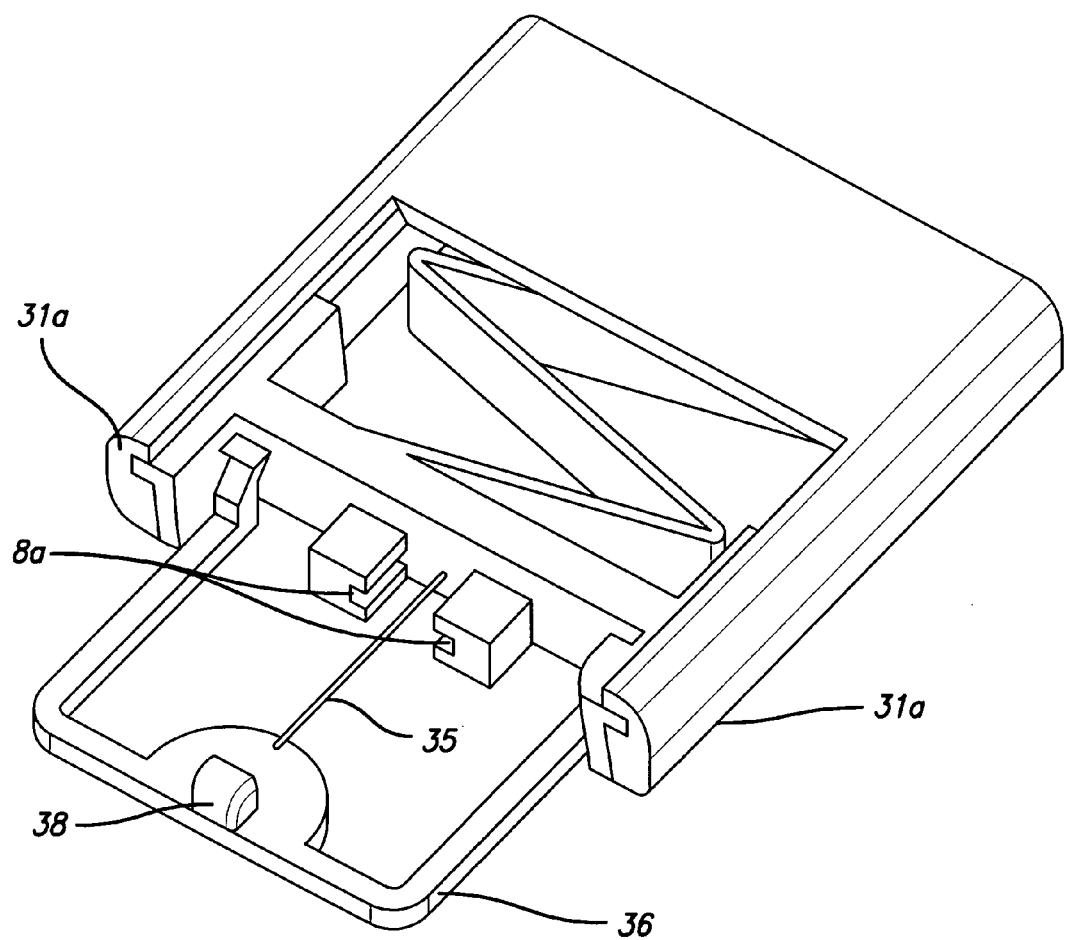
FIG. 9 shows the first embodiment of the injector device where the pivoting member is embracing the needle.

FIG. 6-11 shows a first embodiment of an injector device (29) which can be used for injection of the infusion part (0B) of the infusion set. In FIG. 6 the injector device is separated from the infusion part (0B) and FIG. 7 and 8 show the same injector device (29) joined with an infusion part (0B). The injector device comprises a housing (30) with two longitudinally extending guiding means (31) formed as grooves in this embodiment and a longitudinally slidable member (32) having guiding means (31a), in this embodiment a rim, corresponding to the guiding means (31). A penetrating needle (35) is extending from the front part of the slidable member (32), and the needle (35) is at the end where it is fastened to the slidable member (32) surrounded by guiding means corresponding to the guiding means (13) on the infusion part (0B). The slidable member (32) is capable of moving from a retracted position to a forward position, and is driven from the retracted position to the forward position by a spring (34). The spring is located between the slidable member (32) and the back (33) of the housing. Optionally there is a spring support (37) (FIG. 8) which fits with the back of the housing thereby minimizing the risk of a malfunctioning spring. The injector device further comprises locking means (38) for maintaining the spring in a compressed state and release means (39) for disengaging the locking means. When the locking means (38) are disengaged, the spring (34) drives the slidable member (32) to its forward position, thus introducing the cannula positioned at the front end of the infusion part (0B) into the patient by means of the needle (35). After the introduction of the cannula, the injector device including the insertion needle (35) is withdrawn from the infusion part (0B) leaving the insertion needle in an exposed position. The pivoting member (36) can then be swung into a position where it embraces the needle (35) as shown in FIG. 9.

Figure 10:
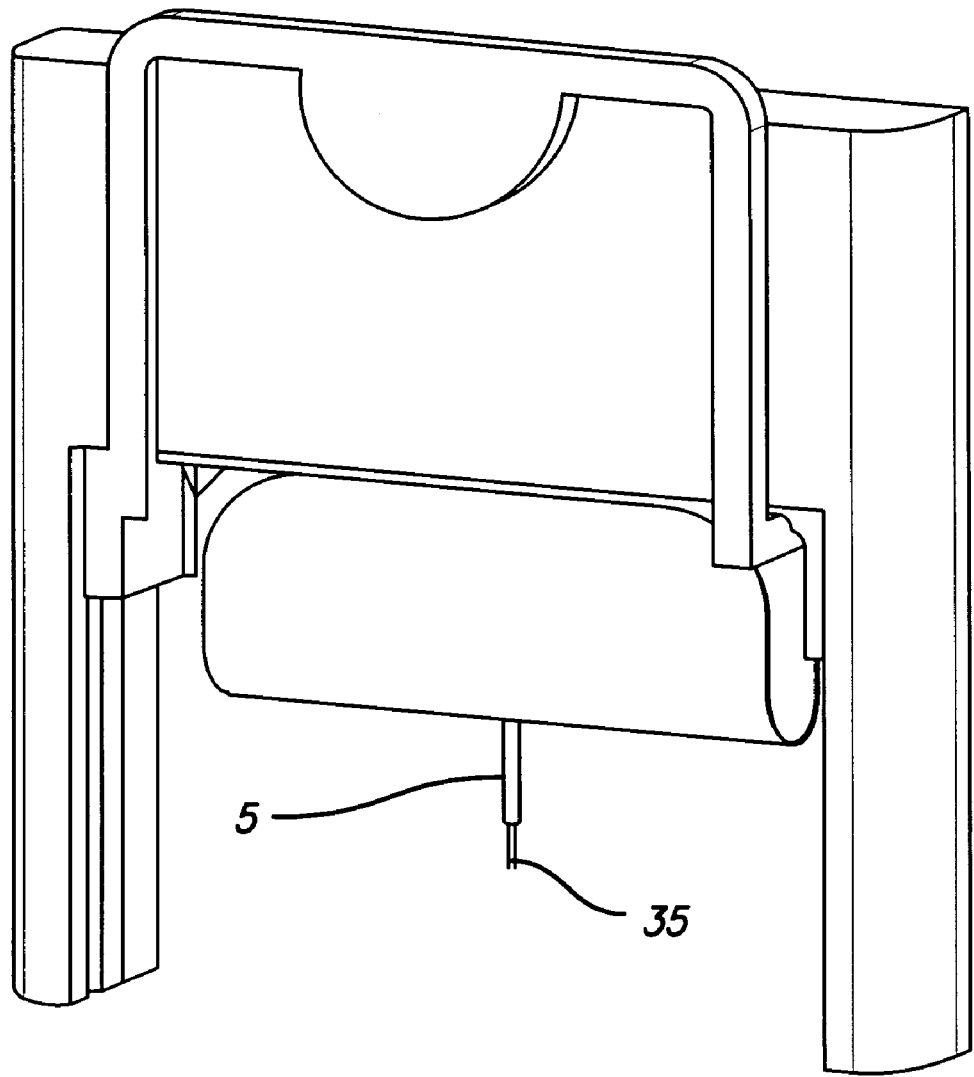
FIG. 10 shows the first embodiment of the injector device in the loaded and secured position before injection.
Figure 11:
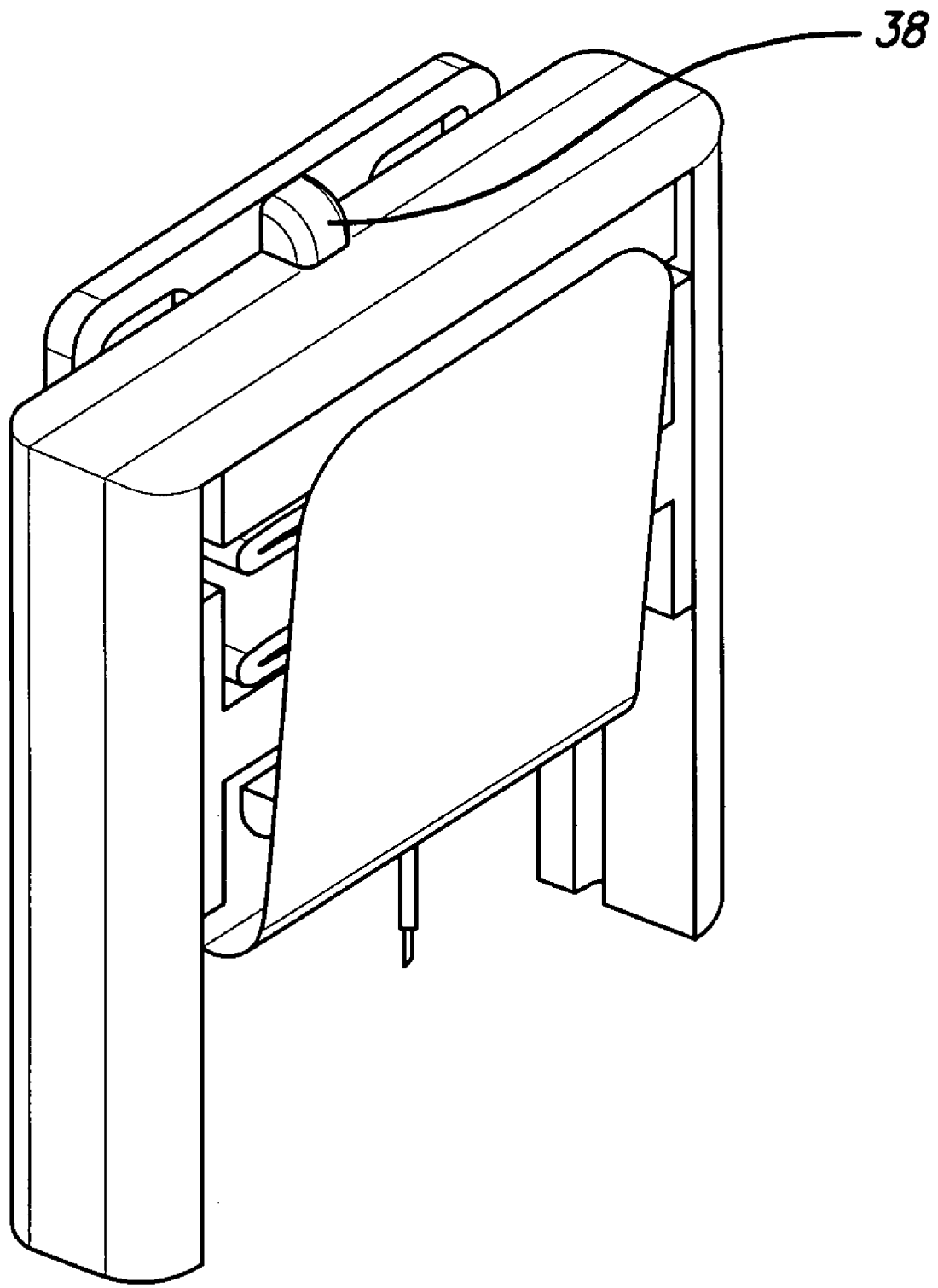
FIG. 11 shows the first embodiment of the injector device in the loaded position from a second angle.

FIG. 10 and FIG. 11 show the same embodiment of the injector device in a loaded and secured position. Part of the pivoting member (36) acts as locking means (38). In FIG. 10 it can be seen how the needle (35) fits into the cannula (5) of the infusion part. The needle (35) will bring the cannula (5) with it during the skin penetration. After penetrating the skin the needle (35) secured to the injector will be withdrawn leaving the cannula inserted in the patient. In FIG. 11 the locking means are shown said locking means are disengaged when the tab (38) is pushed over the edge of the outer side of the back (33) of the housing.

Figure 12:
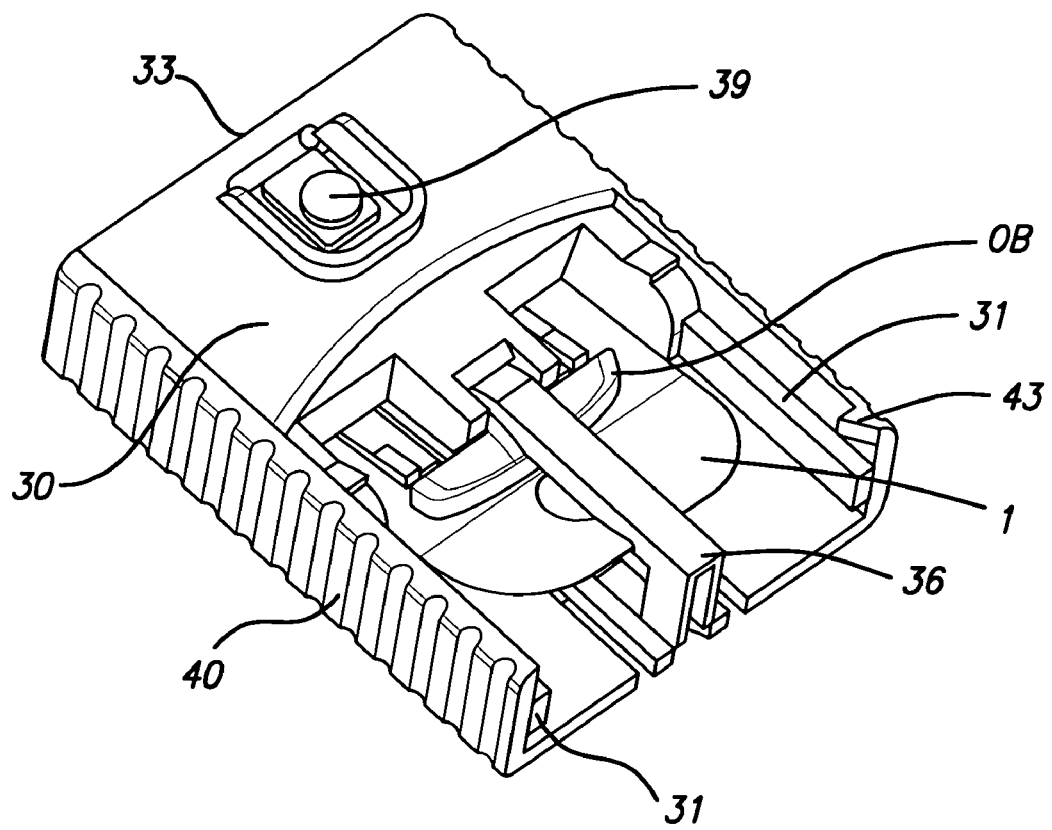
FIG. 12 shows a second embodiment of the injector device in a loaded and secured state.

FIGS. 12 to 17 show a second embodiment of the injector device according to the invention where the pivoting member (36) is fastened centrally in relation to the slidable member (32). FIG. 12 shows the injector device in a state where the pivoting member (36) protects the needle prior to injection of the cannula (5) of the infusion part (0B). The figure shows the housing (30) with another type of longitudinally extending guiding means (31), in this case a bar. The housing further has gripping means (40), preferably in the form of recesses, as means for getting a better grip of the injector device.

Centrally positioned release means (39) is shown on one of the main faces of the injector device. The advantage of a one button release mechanism is that the risk of a slanting injection is reduced.

Figure 13:
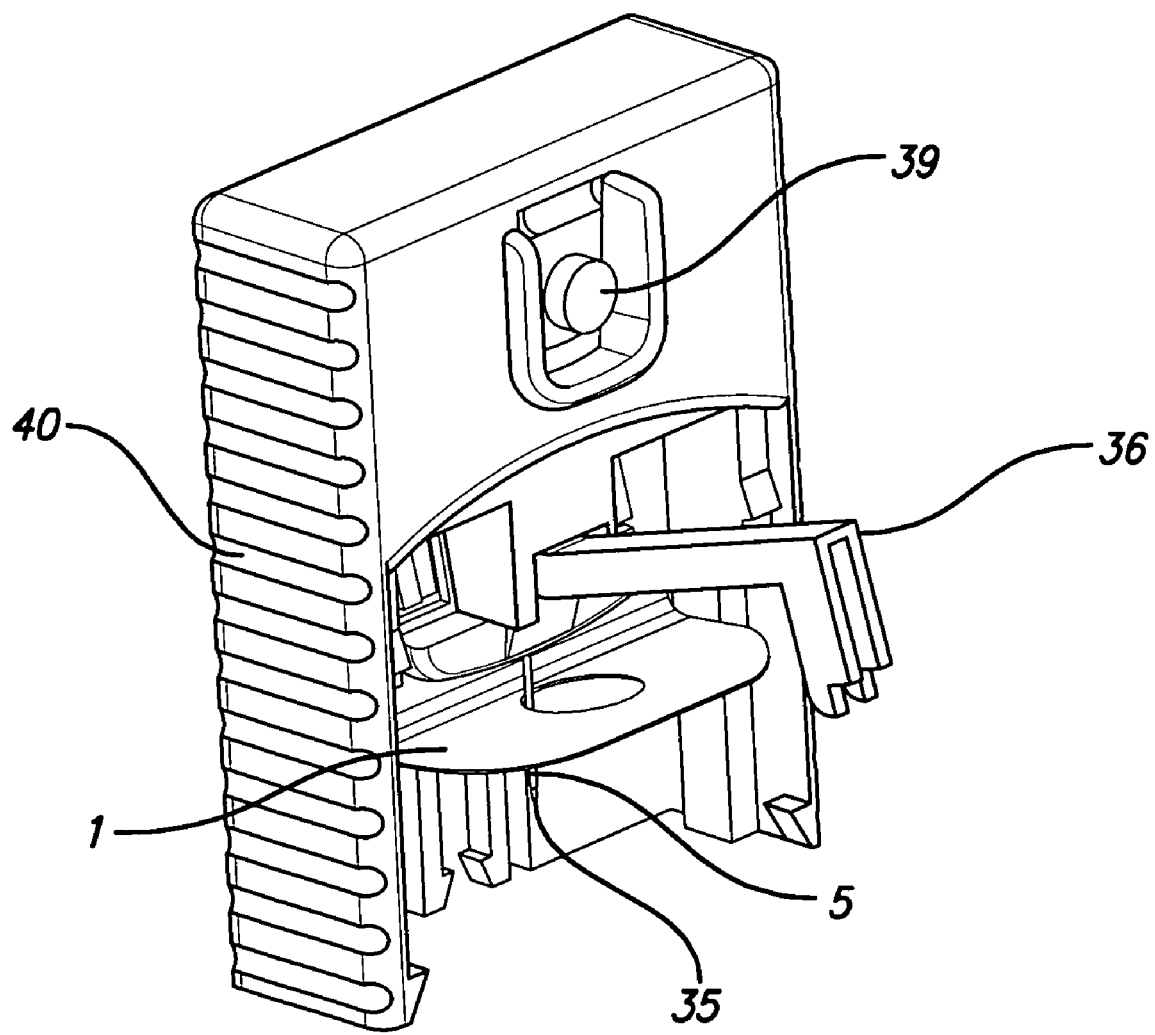
FIG. 13 shows the second embodiment of the injector device in a ready to use state.
Figure 14:
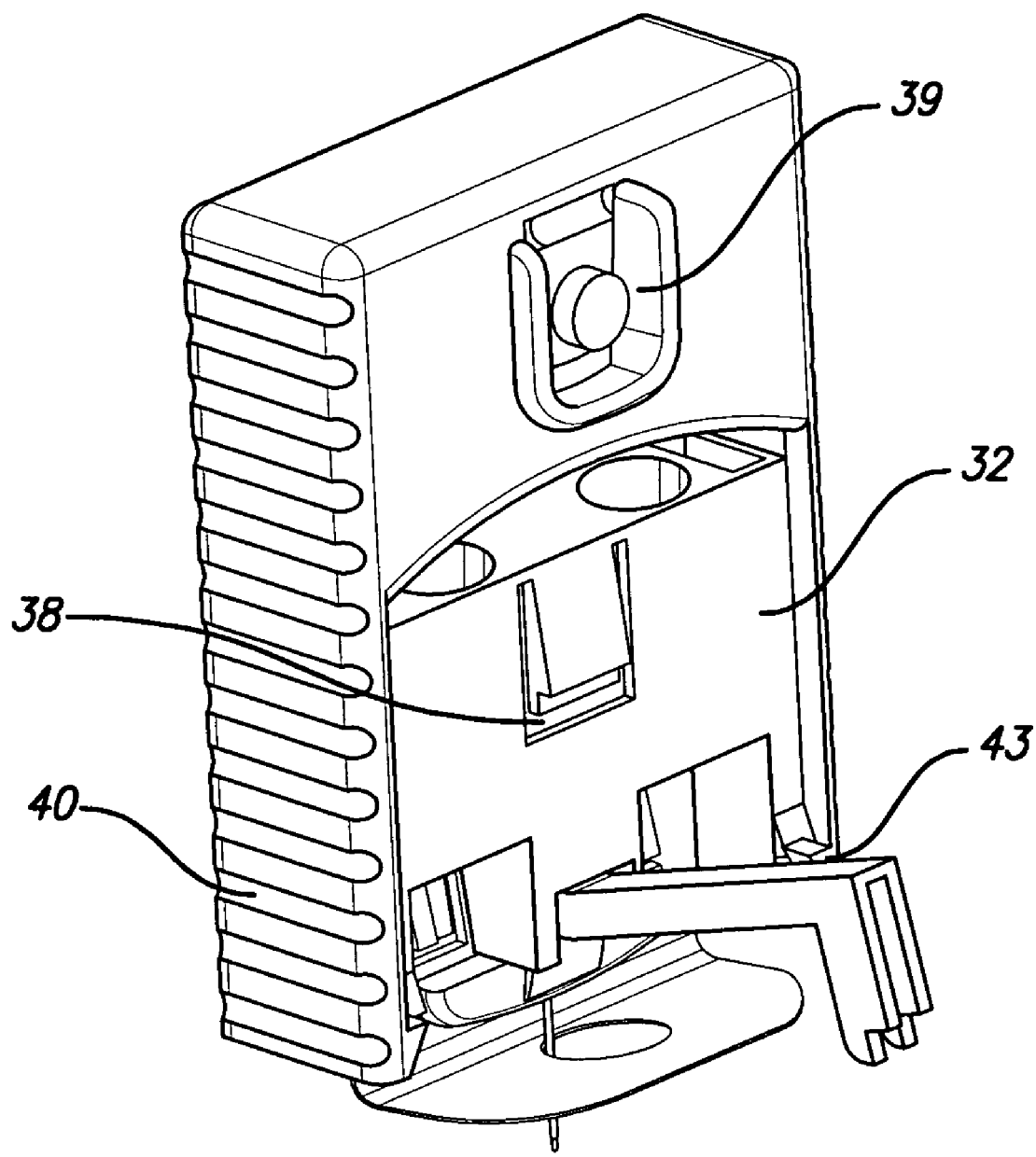
FIG. 14 shows the second embodiment of the injector device after insertion of the needle and before removing the injector from the infusion part.
Figure 15:
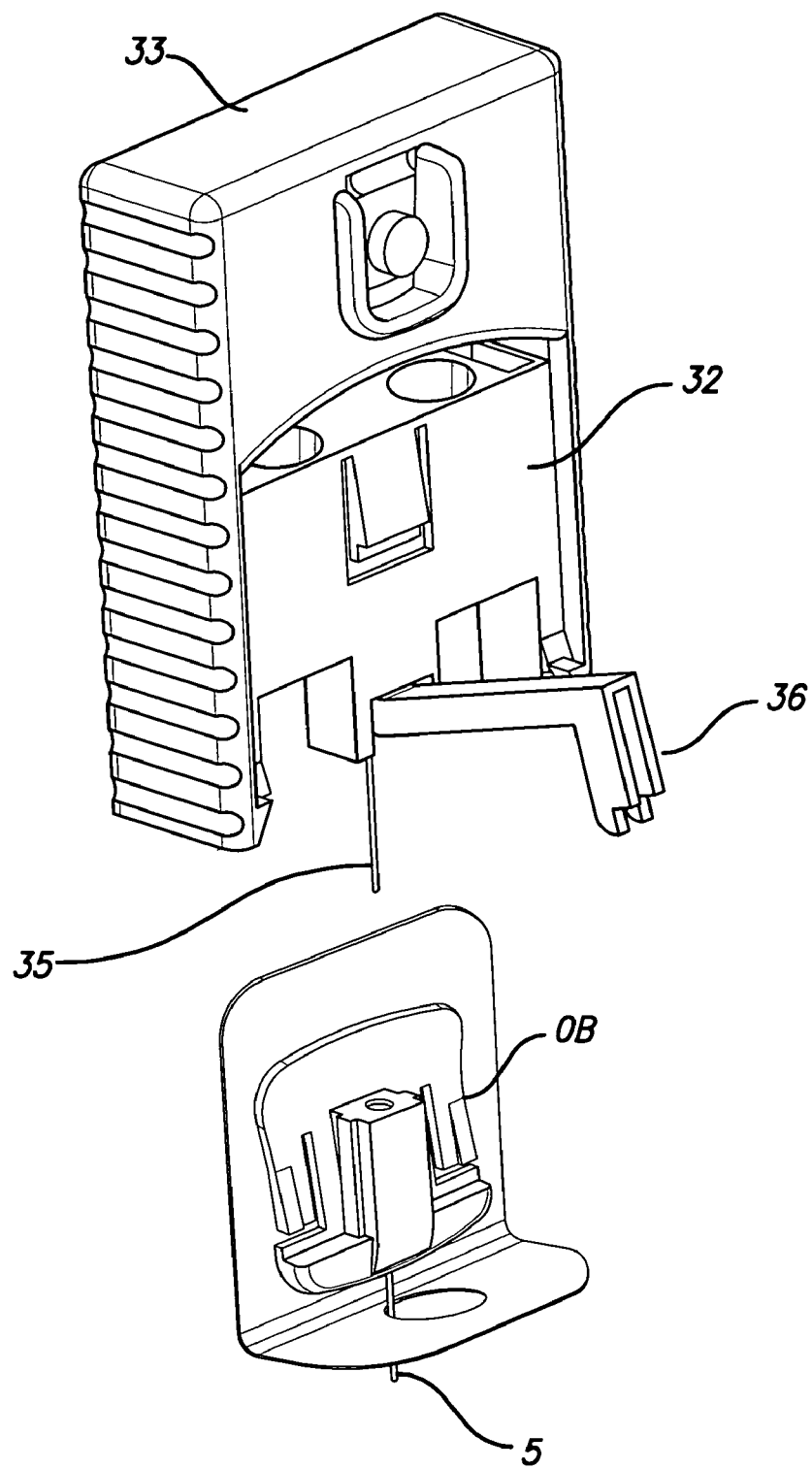
FIG. 15 shows the second embodiment of the injector device after separating the injector from the infusion part.
Figure 16:
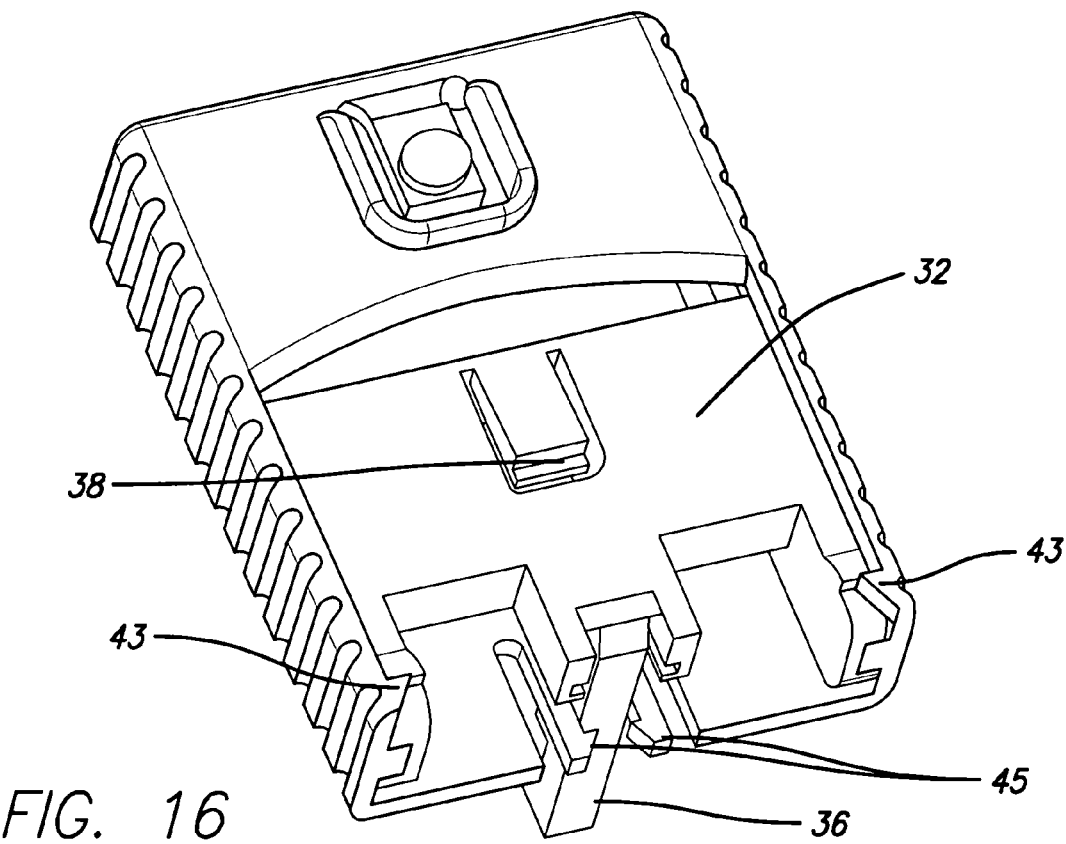
FIG. 16 shows the second embodiment of the injector device after the pivoting arm has been positioned to embrace the needle.
Figure 17:
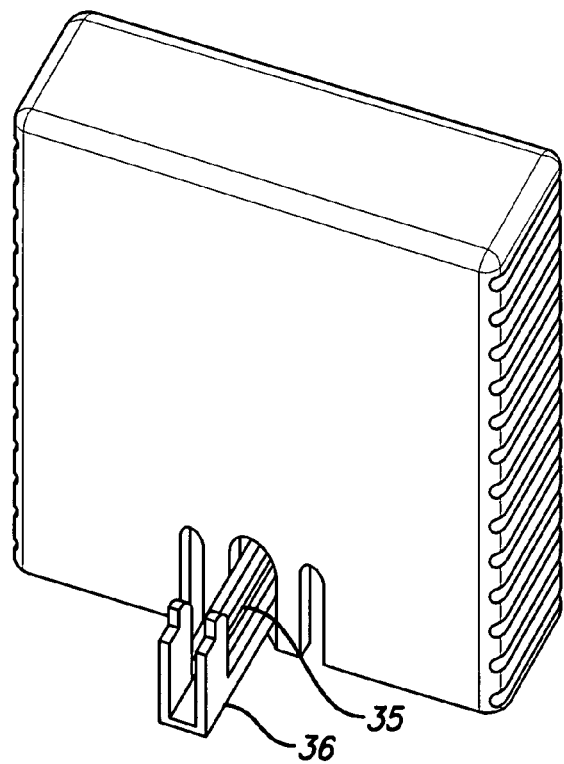
FIG. 17 shows the second embodiment of the injector device after the pivoting arm has been positioned to embrace the needle seen from another angle.
Figure 18:
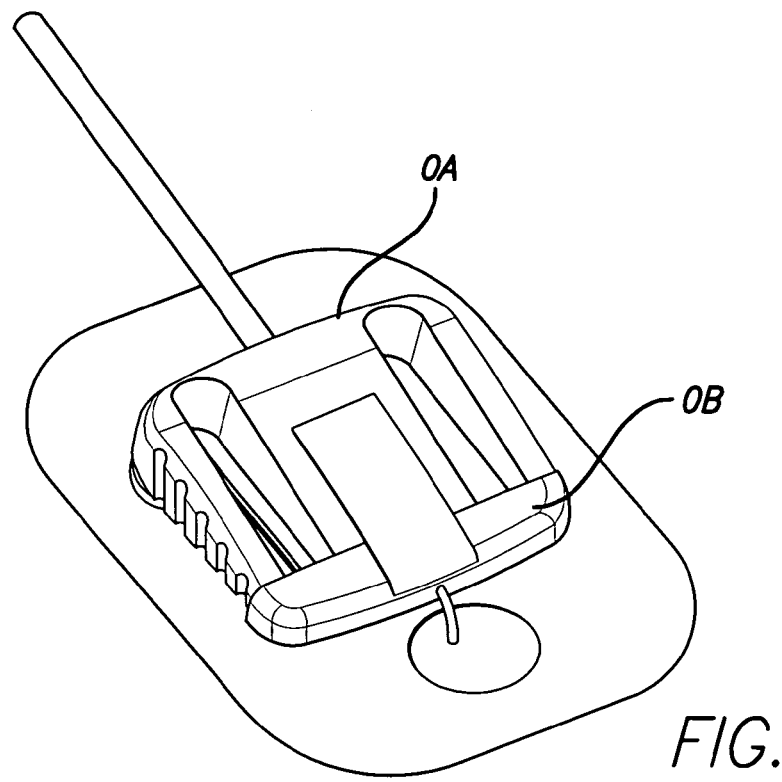
FIG. 18 shows an infusion set placed on the skin.

In FIG. 13 is shown an injector device prepared for insertion of the needle. The pivoting member is positioned away from the embracing position in an angle v≈90° in relation to the main axis of the injector device where the main axis is coincident with the insertion needle. The adhesive support (1) is positioned in such manner that the cannula (5) of the infusion part (0B) and the therein positioned needle (35) penetrates the adhesive support through an opening in the release liner. When the pivoting member is positioned essentially perpendicular to the main plane of the injector device it can provide a helping mean for achieving essentially vertical injection of the needle. Further FIG. 13 shows the needle (35) of the injector device inside the cannula (5). In FIG. 14 the injector device is in a released state where the needle (35) would have penetrated the skin. The housing in the embodiment of FIG. 14 has a stopping tab (43) corresponding to a protrusion on the slidable member that keeps the slidable member (32) within the housing (30) thereby making it easier to withdraw the needle since there is no risk that the slidable member slides out of the housing. In FIG. 15 the injector device has been withdrawn, leaving the cannula (5) of the infusion part (0B) inserted in the patient. In FIG. 16 and 17 the pivoting member (36) is in a position where it embraces the needle (35) thereby protecting the surroundings from coming into contact with the used needle (35). In FIG. 18 the infusion part (0B) has been brought from the essentially vertical insertion position to a position essentially parallel to the skin.

Figure 19:
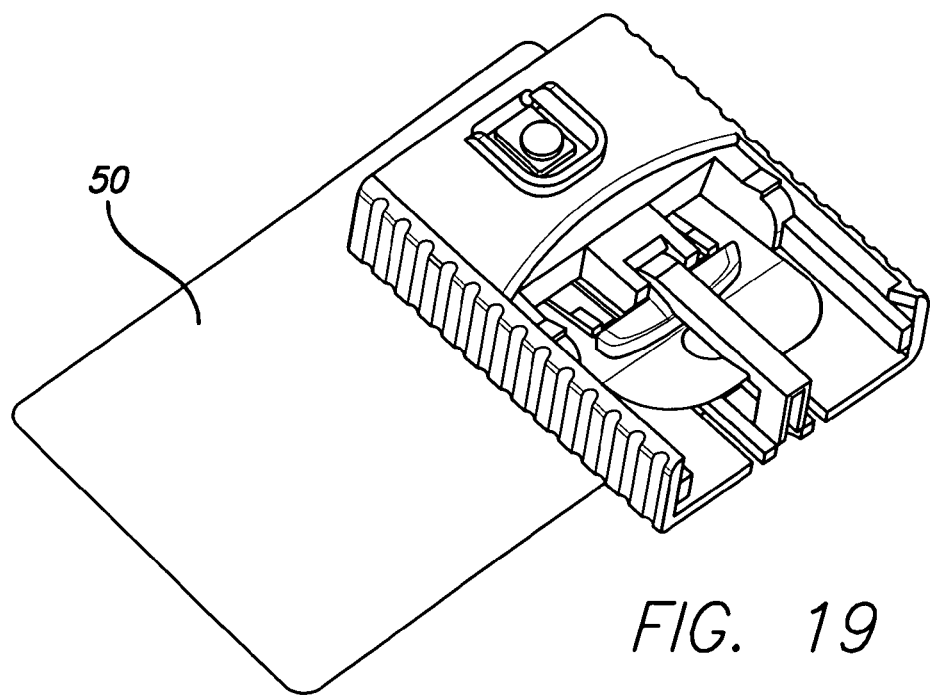
FIG. 19 shows the second embodiment of the injector device together with a credit card.

FIG. 19 shows the injector device together with a credit card to illustrate the size of the injector device.

Figure 20:
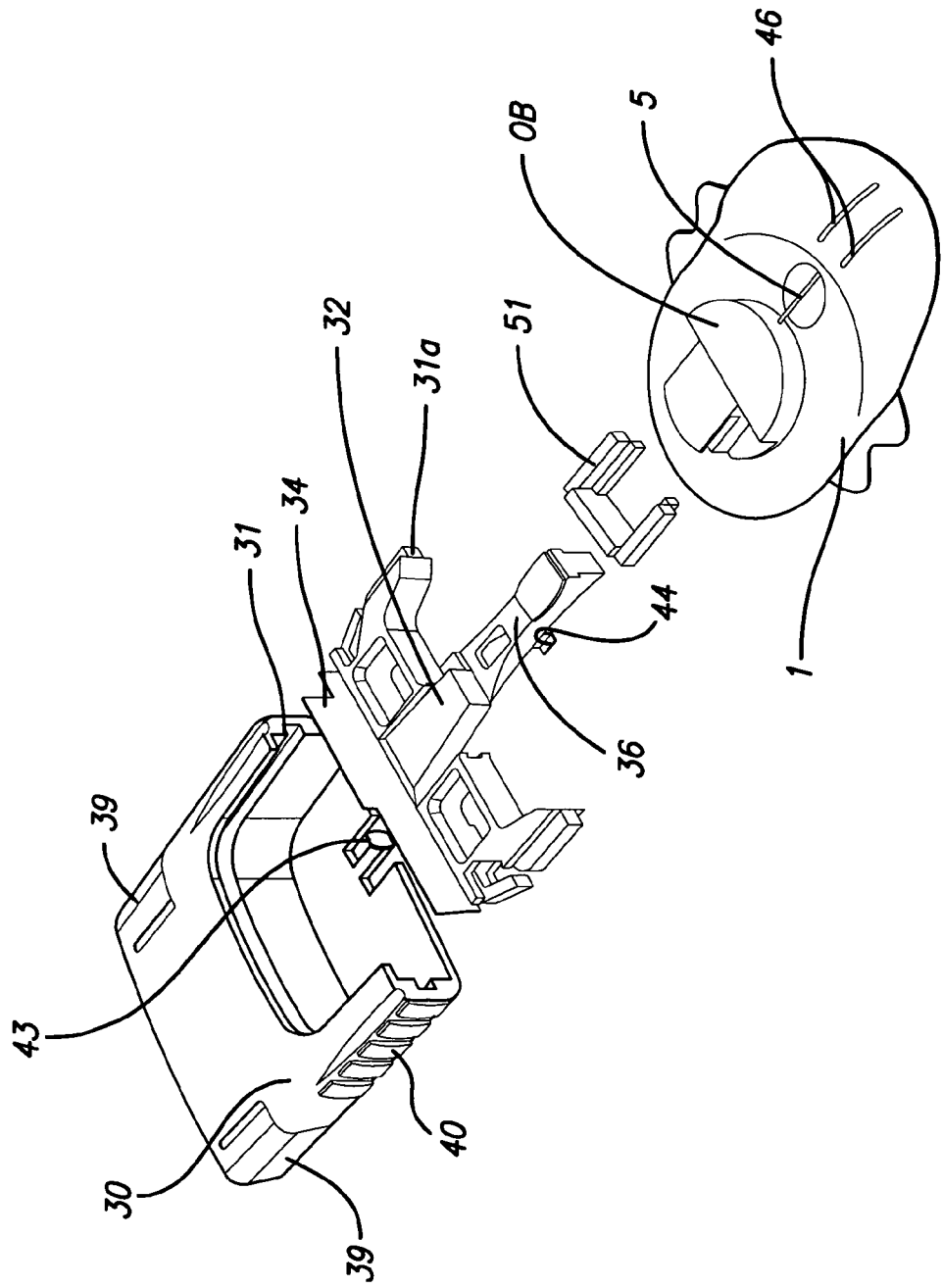
FIG. 20 shows a third embodiment of the injector device.
Figure 21A:
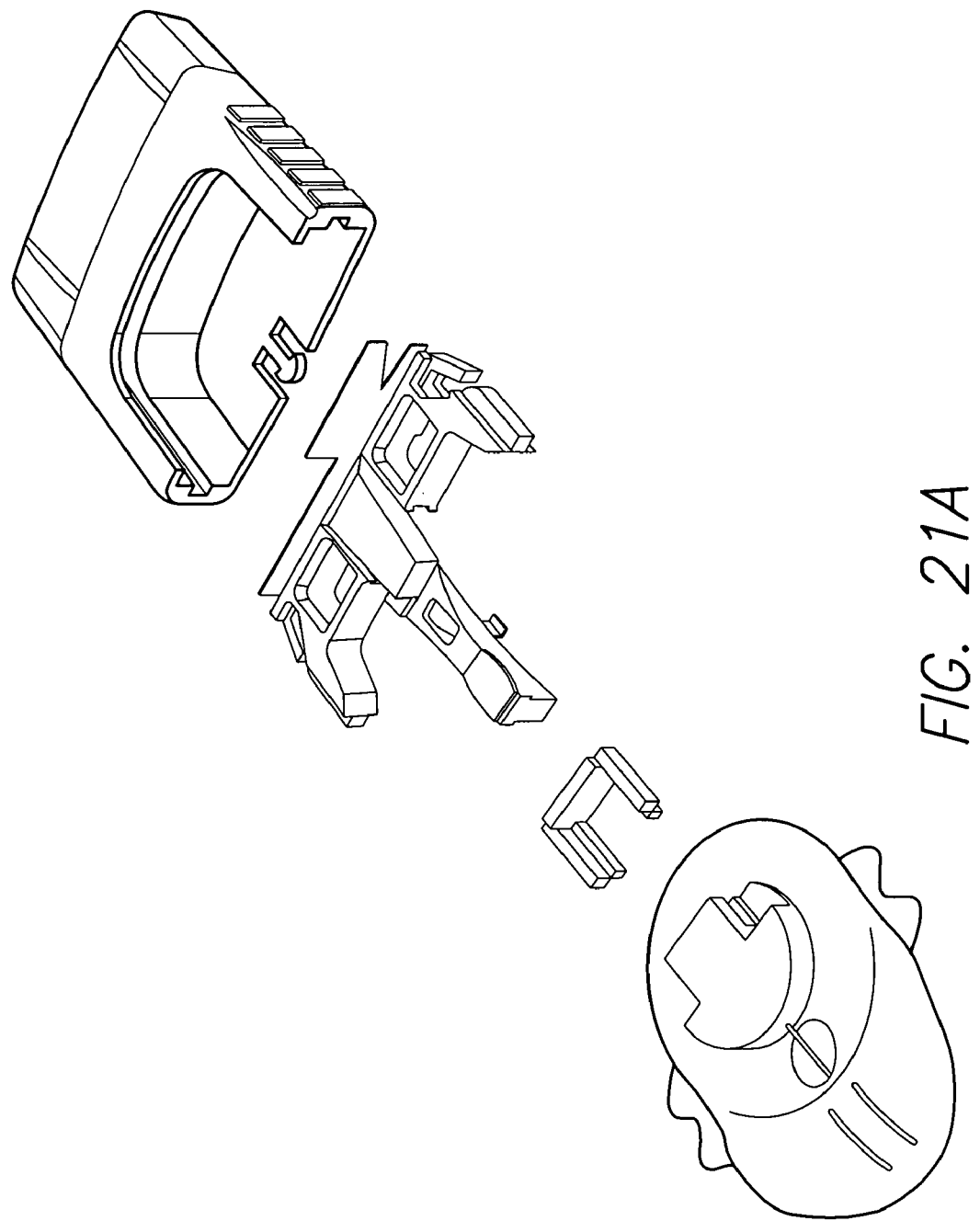
Figure 21B:
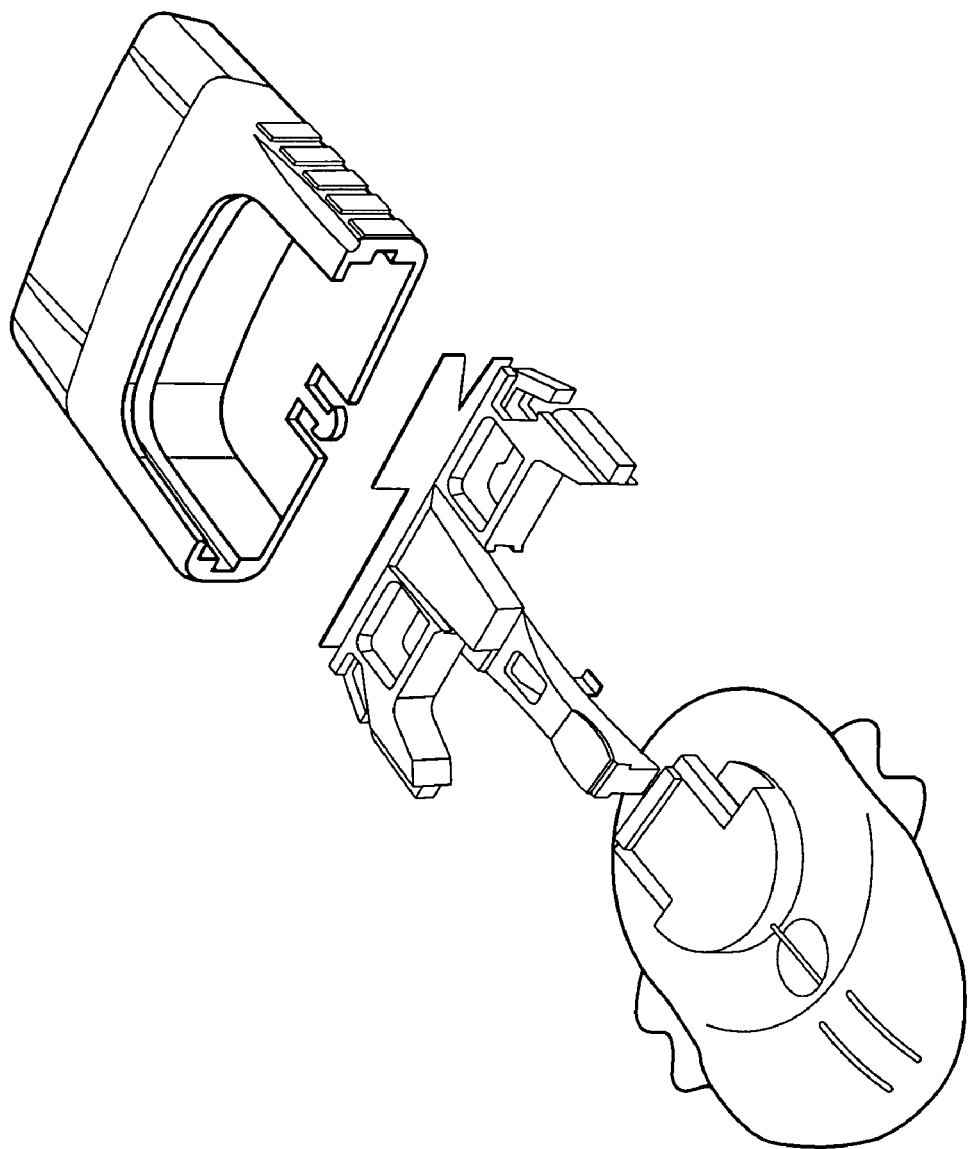

In FIG. 20 is shown a third embodiment of the injector device together with an infusion part (0B). This embodiment also has a housing (30) with longitudinally extending guiding means (31) and a longitudinally slidable member (32) of a different construction compared to the two first embodiments. Also the pivoting arm (36) and the spring (34) can be seen in this figure. In this embodiment the stopping tab (43) is placed centrally and has the form of a protrusion raising form the lower side of the housing (30). The release means (39) comprises two buttons placed on each side of the housing (30).

In FIG. 20 and FIG. 21A-D it is shown how the infusion part (0B) along with the slidable member (32) and the spring (34) of the third embodiment fit into the housing (30). The unit (51) shown between the pivoting arm (36) and the insertion part (0B) is an adapter which makes it possible to use a standartd injector for different guiding means (13) on the infusion part (0B).

Figure 22A:
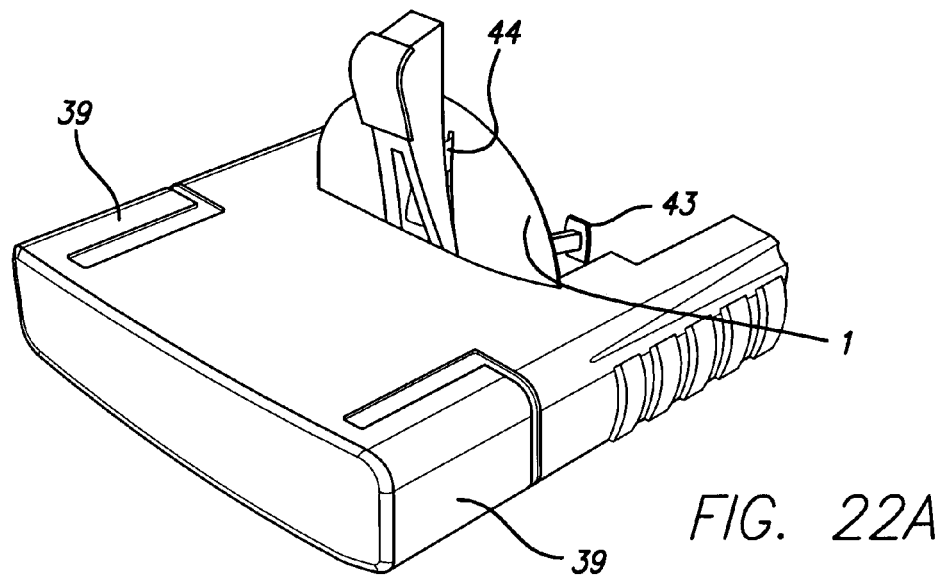
FIG. 22A-B shows the third embodiment of the injector device prepared for insertion.
Figure 22B:
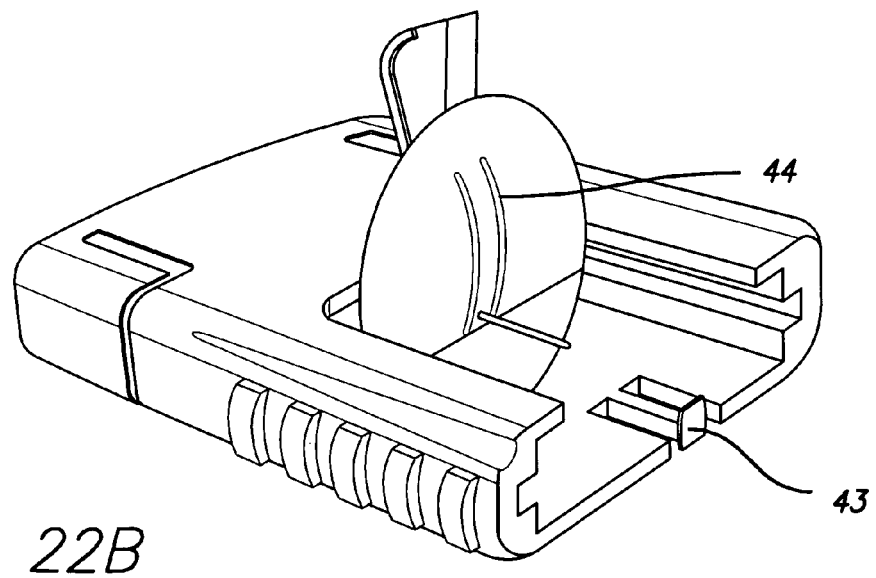

In FIG. 22A-B is shown fixing means (44) placed on the pivoting member (36). It is possible to temporarily attach a part of the adhesive support (1) to the fixing means in order to secure the position of the adhesive support in such a way that the adhesive surface of the support (1) will be turned towards the skin of the patient. Further release means (39) in the form of two buttons, one on each side of the housing (30), can be seen as well as the protruding stopping tab (43).

FIG. 23A-B shows in further details and without the housing how the adhesive support (1) is hooked to the fixing means (44) due to at least one cutting (46) in the adhesive support (1).

Figure 24A:
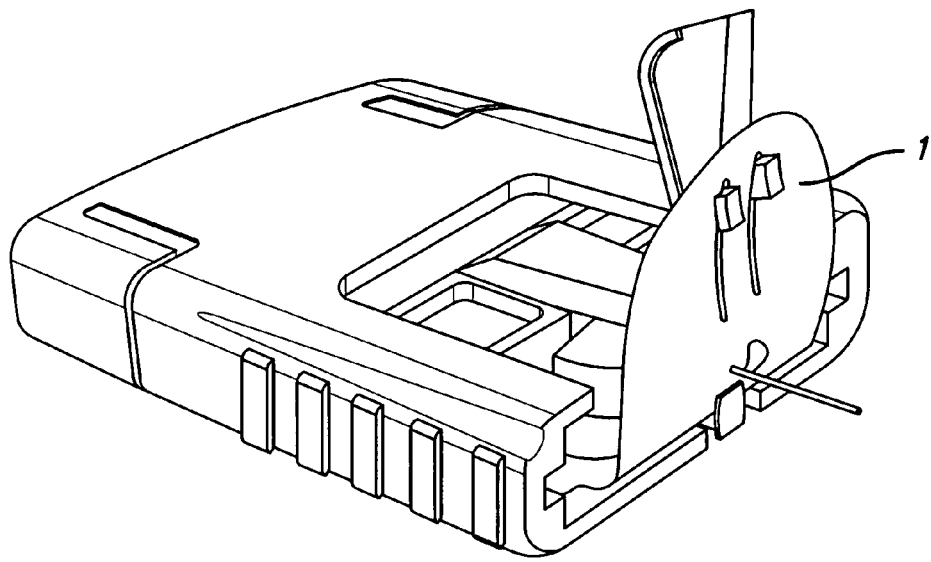
FIG. 24A shows the injector device after insertion with an infusion part and FIG. 24B shows the injector device after insertion without the infusion part.
Figure 24B:
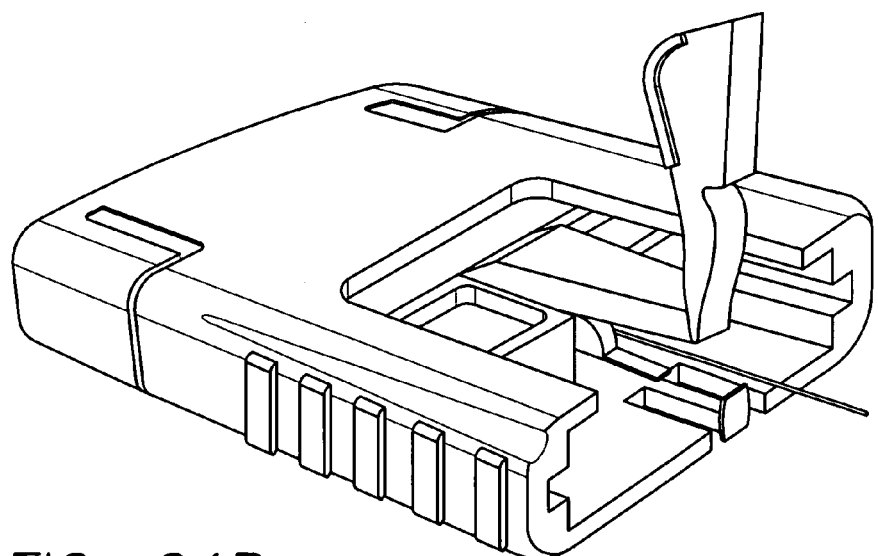

FIG. 24A shows the third embodiment of the injector device with an infusion part after insertion and 24B shows the injector device after insertion and after the injector device has been removed from the insertion part (0B).

Figure 25:
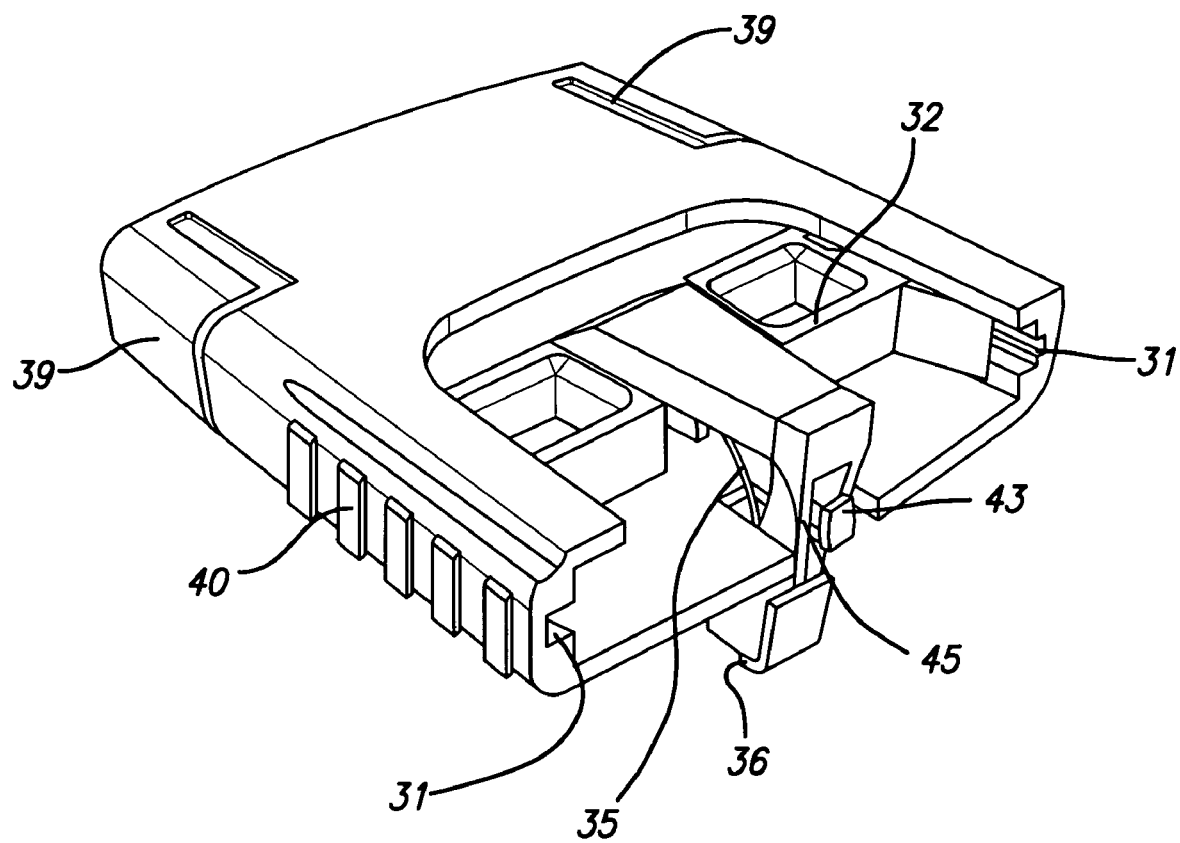
FIG. 25 shows the third embodiment of the injector device after insertion and embracing the needle.

In FIG. 25 the pivoting member (36) of the injector device is in a position embracing the needle. A locking tab (45) fixes the pivoting arm in this position. This makes certain that the needle stays embraced by the pivoting arm and thereby minimizes the risk of somebody getting hurt by the needle.

Figure 26:
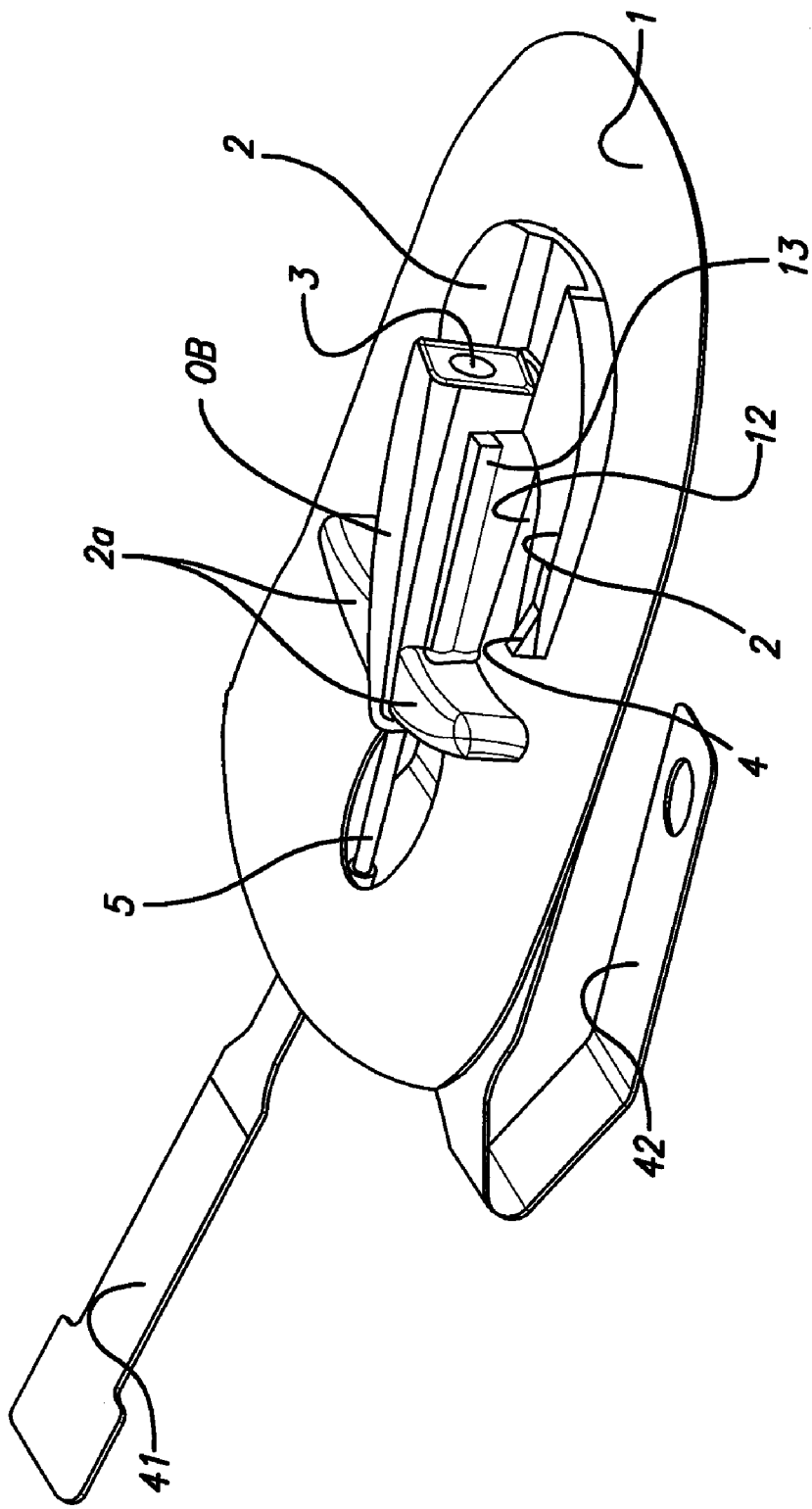
FIG. 26 shows a third embodiment of an infusion part placed on a mounting pad with two separate pieces of release liner.

FIG. 26 illustrates a third embodiment of an infusion part (0B). The infusion part (0B) comprises a base part (2) which base part (2) comprises a first set of guiding means (13) in the form of two stabilizing fins. The base part (2) comprises two retention devices (4) extending from the upper surface of the base part (2) and having a triangular form. The side of the triangular retention device facing the shoulder part (2a) is approximately perpendicular to the surface of the base part (2) and the side facing away from the shoulder part (2a) is sloping from the top of the retention device (4) to the surface of the base part (2). Mounted on the inner surface of the infusion part (0B) is the adhesive support (1). The cannula (5) is extending from the shoulders (2a) of the base part (2) and is penetrating the adhesive support (1) being in fluid communication with the central cavity (3). The cavity (3) which can be covered by a membrane is adapted to receive a second cannula (6) extending from the connector. In this embodiment the base part (2) has two wide cuttings (12) creating two narrow flaps in the base part (2) on which the retention devices (4) are mounted.

The distance between (I) the side of the retention device (4) closest to the central part of the infusion part (0B) and (II) the central part of the infusion part (0B) defines how far it is possible to move the two arms (9) of the connector in the plane parallel to the base part (2). It is necessary for the corresponding means (10) in the arms (9) of the connector (0A) to be of less width than the distance between (I) and (II). In a preferred embodiment it would also be possible to free the connector (0A) from the infusion part (0B) by moving the arms (9) in a vertical direction away from the base part (2). If this should be possible the arms (9) of the connector need to be adequately flexible where the arms (9) are fixed to the central part of the connector. This can be done either by reducing the thickness of the arms (9) in at least on direction in this area until the desired flexibility is achieved or by choosing to construct the connector part (0A) of a material with a suitable flexibility.

In this embodiment the release liner (41, 42) of the adhesive support (1) is divided into to separated pieces. The first piece (41) is protecting the part of the adhesive support (1) in front of the cannula (5), and the second piece (42) is protecting the part of the adhesive support being behind the cannula (5) and under the infusion part. During insertion the two pieces are separated whereby the part of the adhesive in front of the cannula is bent up and the adhesive side of the adhesive support (1) is exposed around the cannula. The first piece (41) is either pulled back by the user or is attached to one side of the injector device; the second piece (42) is attached to the opposite side of the injector device.

In FIG. 26A-D the cycle of use for the injector device is illustrated.

Figure 26A:
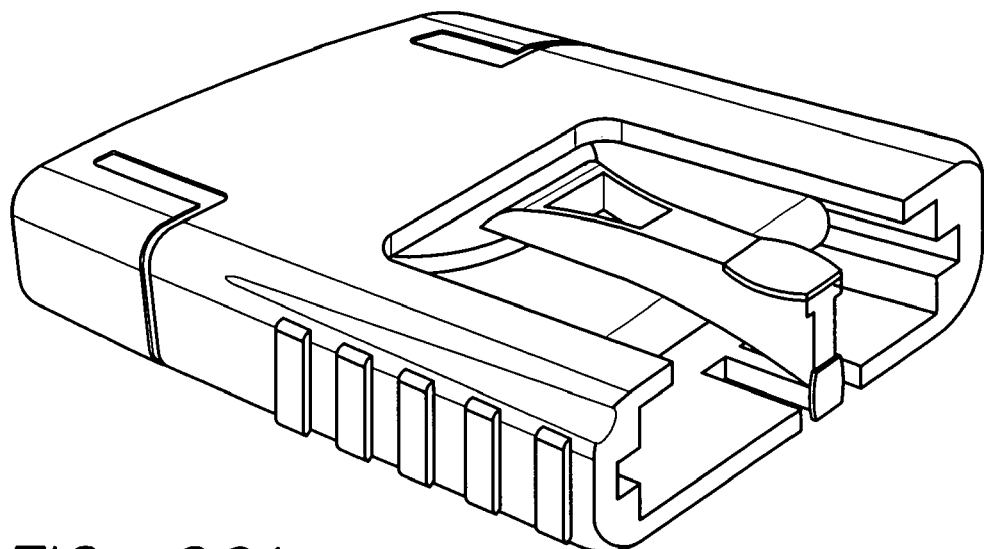
FIG. 26A-D shows the different steps when injecting the infusion part.
Figure 26B:
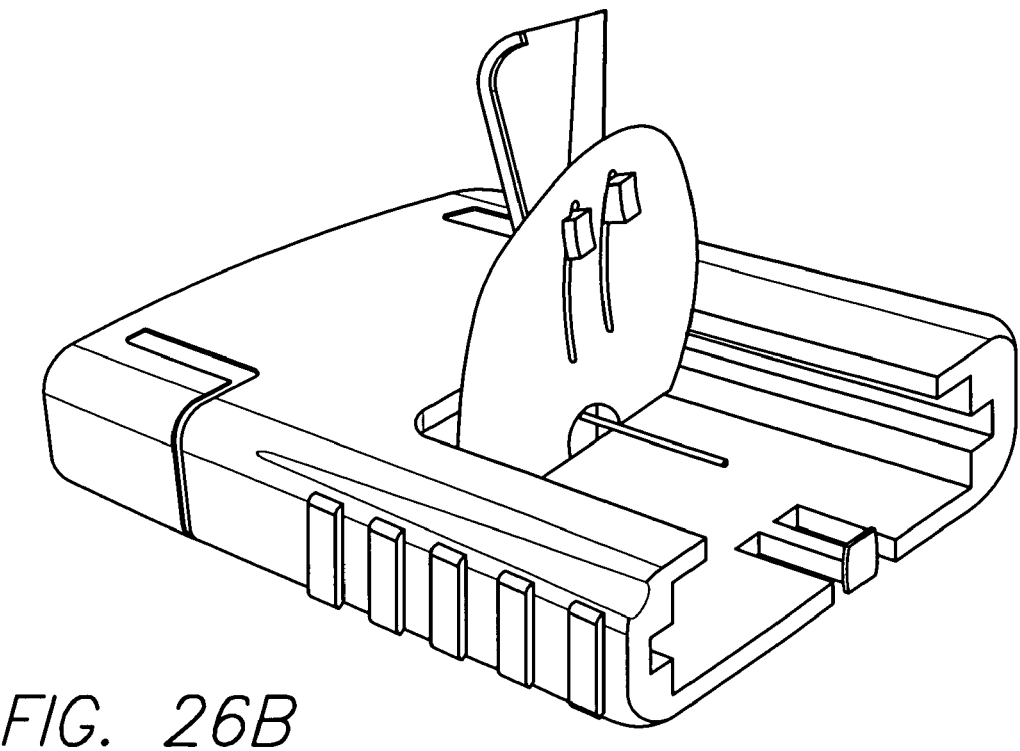
Figure 26C:
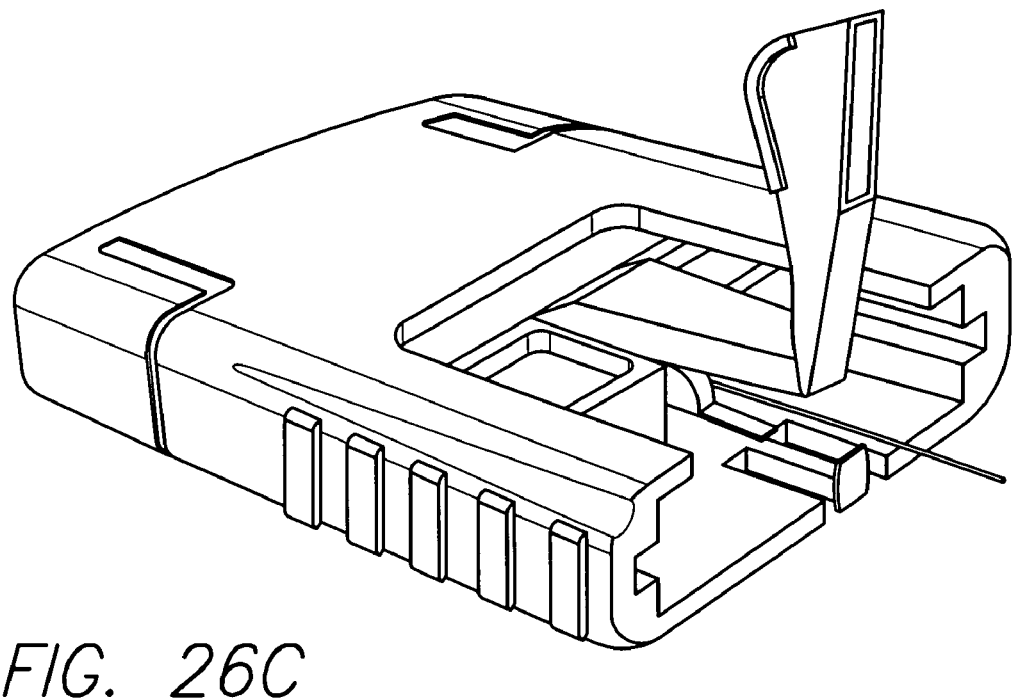
Figure 26D:
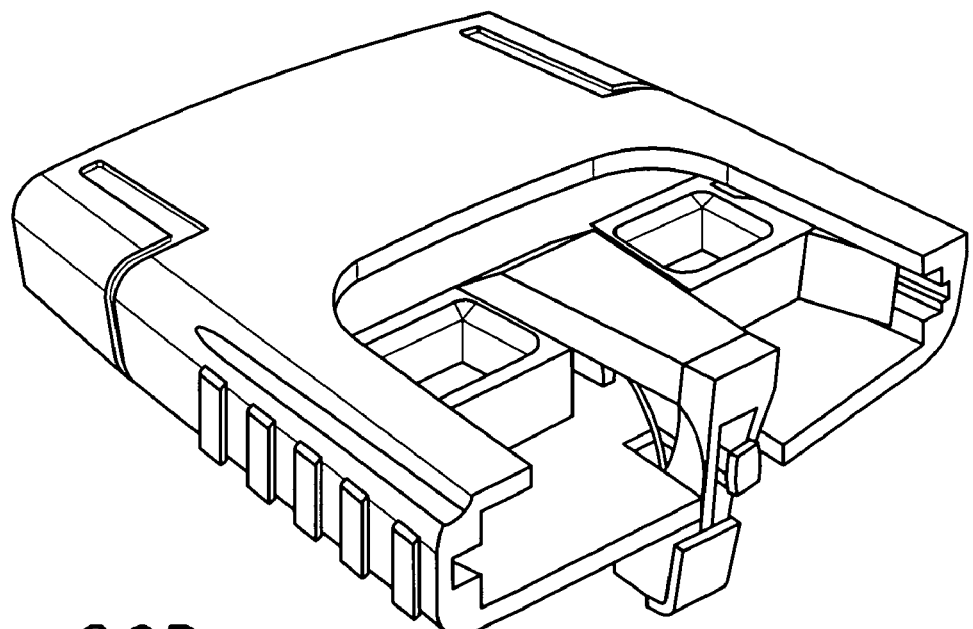

When the infusion set is delivered to the patient together with the injector device, the infusion part (0B) and the connector (0A) are packed separately and under sterile conditions, and the infusion part (0B) is placed in the injector device (FIG. 26A). When the user wants to insert the infusion part (0B), the user pulls the pivoting arm and turns the arm perpendicularly to the housing (30) (FIG. 26B). In this position the needle (35) placed on the slidable member (32) is exposed and the adhesive support is bend backwards with the adhesive surface turned towards the users skin. The user then pushes the buttons (39) on each side of the housing which releases the spring and pushes the slidable member (32) towards the user's skin (FIG. 26C). The needle (35) will in this position penetrate the skin and place the cannula of the infusion part (0B) subcutaneous. After placing the infusion part (0B) the injector device is removed, and in order to protect the surroundings from the used needle (35) the pivoting arm (36) is turned approximately 180° to an angle w≈90° perpendicular to the main axis of the injector device, where it embraces the needle and make it safer to dispose of the device.

FIGS. 27A-E and 28A-E also illustrates the cycle of use of the injector device seen respectively from the upper (FIG. 27) and the lower (FIG. 28) side of the injector device.

Figure 27A:
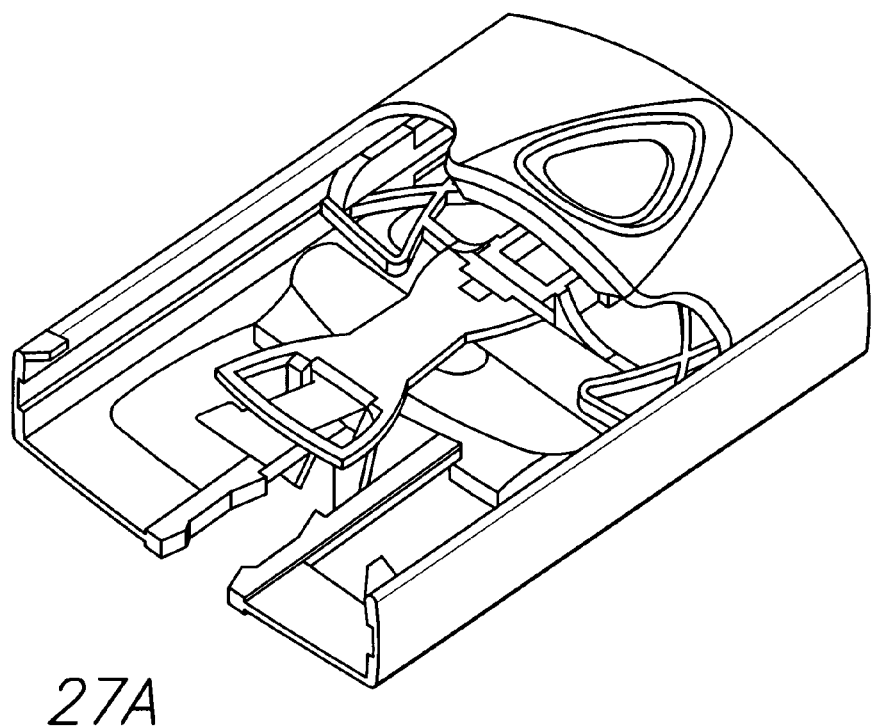
FIGS. 27A-E and 28A-E show the different steps when using the injector device for injecting the infusion part.
Figure 28A:
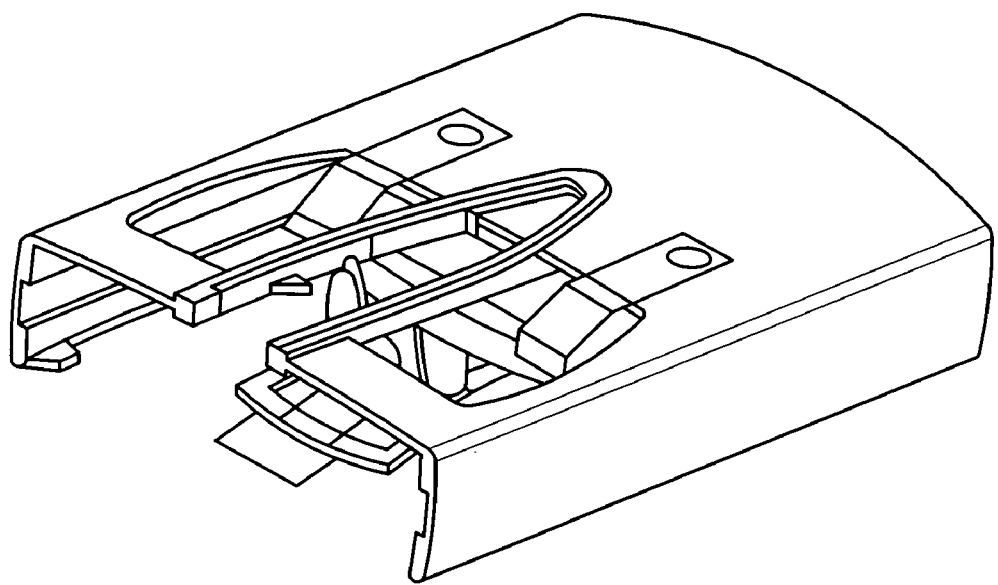

In FIGS. 27A and 28A the device is in a first state, which is the state the device would normally be delivered to the patient in, under sterile conditions. In this state the pivoting arm (36) is in a position where it embraces the needle (35) and the angle v between the main plane of the injector device and the pivoting arm is approximately 0°, if the release means (39) should unintentionally be pressed in this situation two protruding tabs (48) will prevent the slidable member (32) from being pushed forward.

Figure 27B:
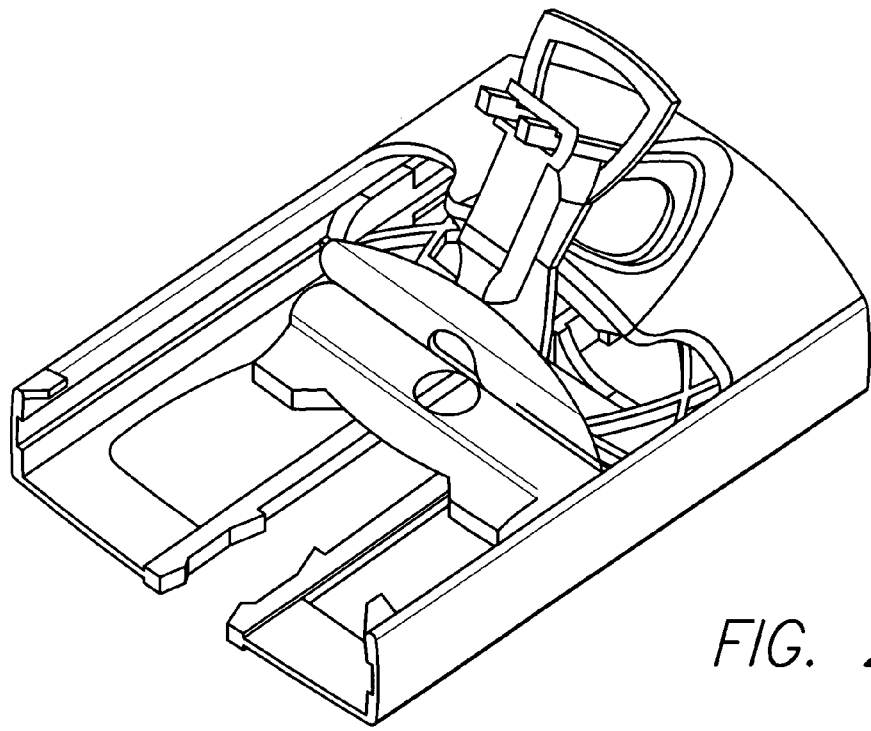
Figure 28B:
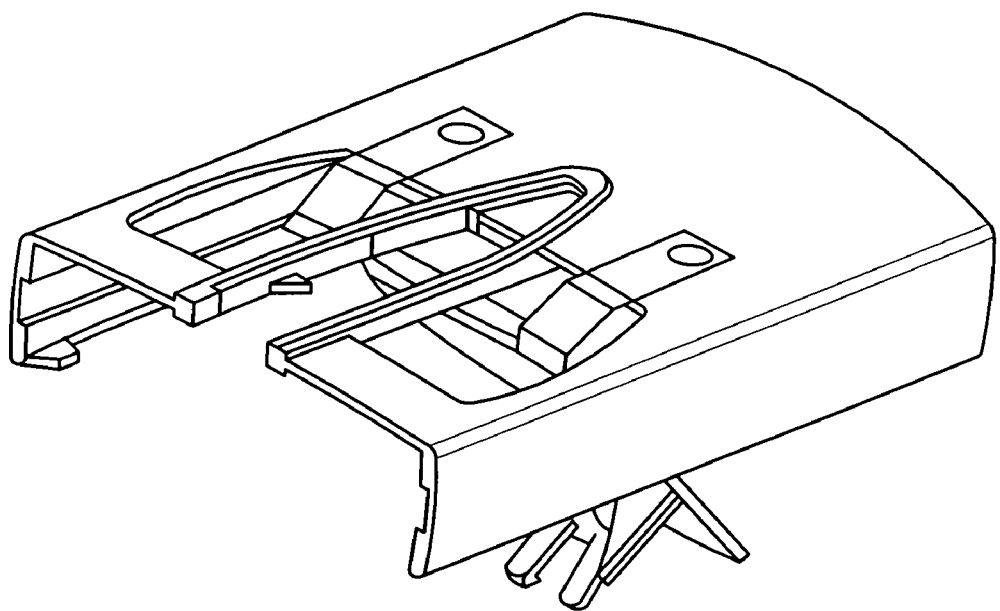

In FIGS. 27B and 28B the device is prepared for use by lifting the pivoting arm (36) backwards thereby exposing the insertion needle (35) and also in this embodiment lifting the part of the release liner (41) which is attached to the pivoting arm (36), exposing the underlying adhesive support (1). In this position the pivoting arm (36) allows for insertion of the needle and is in an angle v to main plane of the injector device where 90°≦v≦180°, and in this position the injector device would be placed against the patient's skin.

Figure 27C:
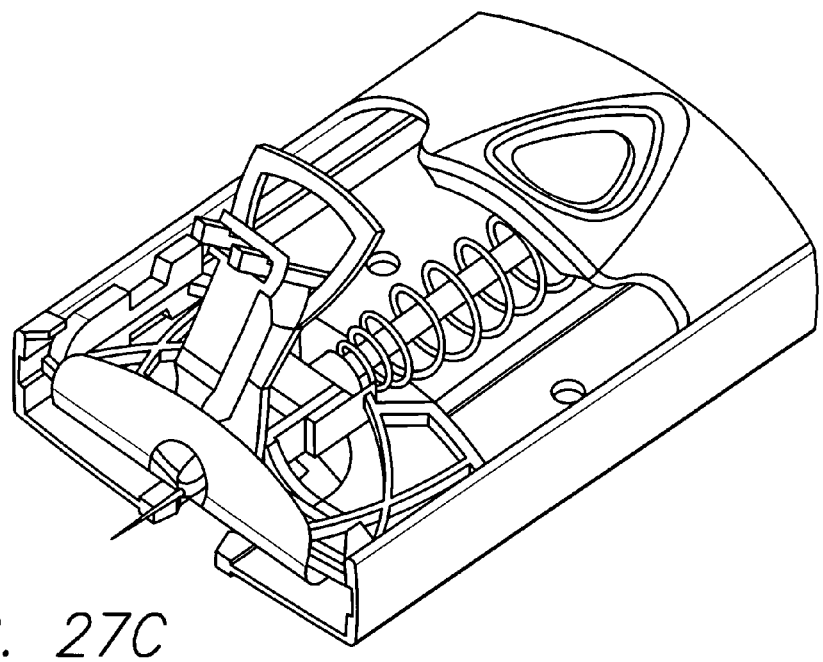
Figure 28C:
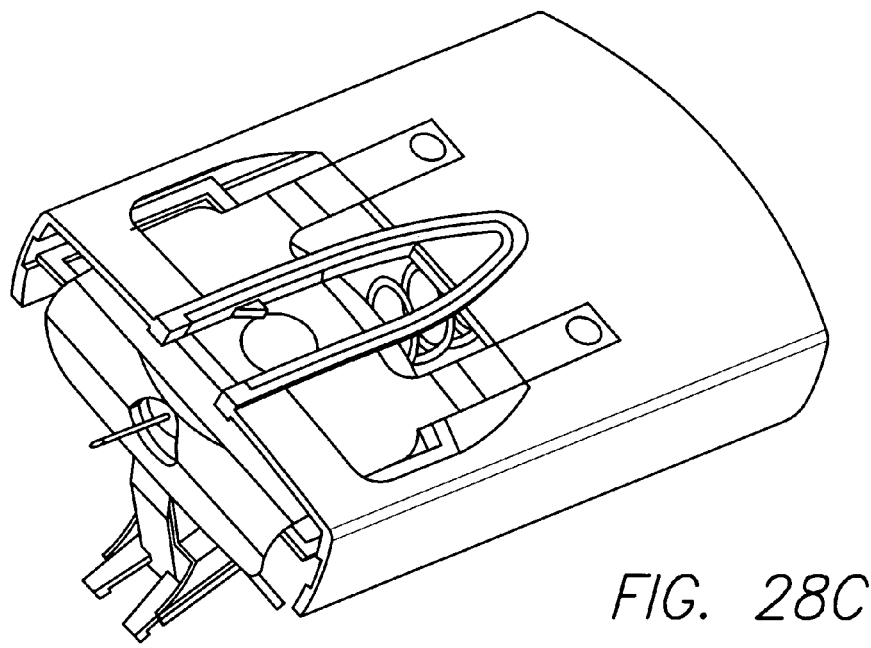

In FIGS. 27C and 28C the release means (39) has been pressed and has released the spring (34). The spring has pushed the slidable member (32) forward until the slidable member was stopped by two stopping tabs (43). In this position the insertion needle (35) has penetrated the patient's skin and a part (this part covers an area around the needle in the full breadth of the adhesive support) of the adhesive surface of the adhesive support (1) is in contact with the patient's skin. In FIG. 28C it is shown how the second part (42) of the release liner is attached to the housing (30) and still covers the adhesive surface when the slidable member (32) is pushed forward.

Figure 27D:
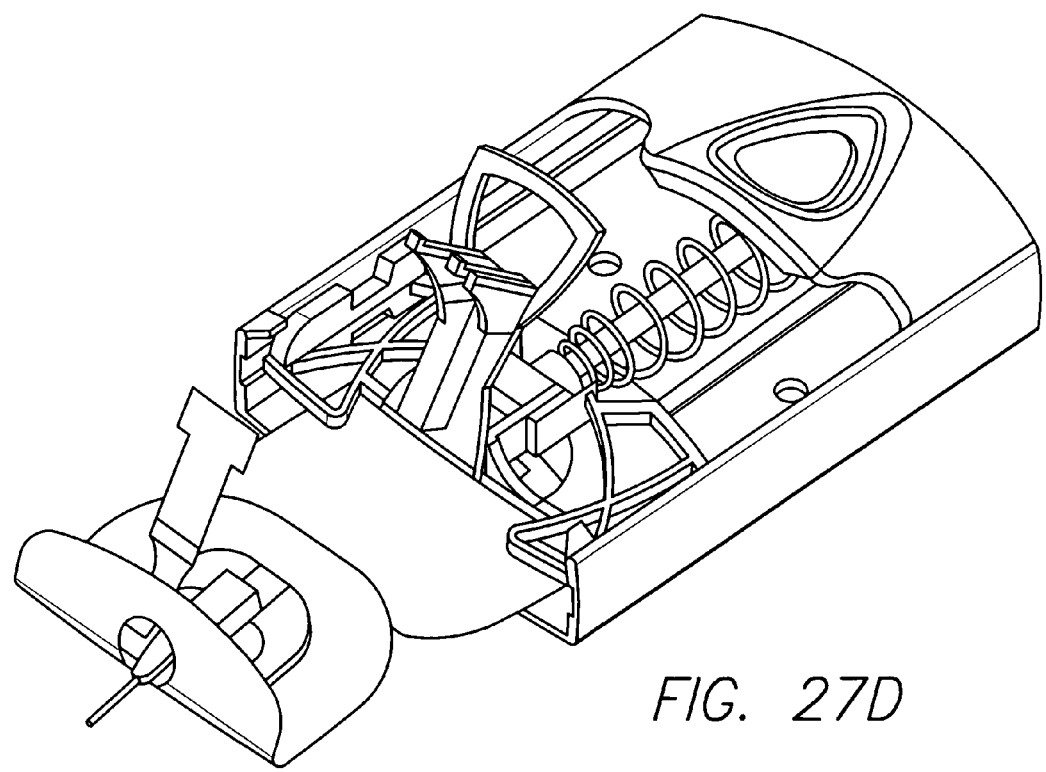
Figure 28D:
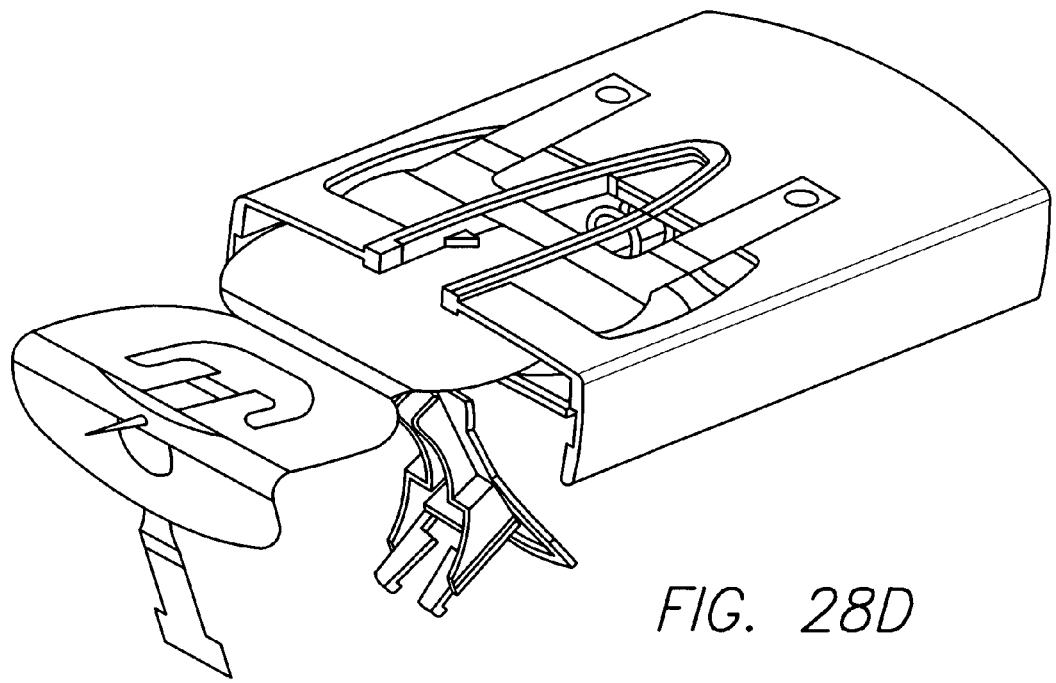

In FIGS. 27D and 28D it is shown what happens when the injector device is removed from the patient, leaving the infusion part (0B) inserted subcutaneously. The user frees the first part (41) of the release liner from the pivoting arm (36) and then when pulling the injector device away the second part (42) of the release liner is also pulled away, exposing the adhesive surface of the adhesive support (1) and making it possible for the user to press the adhesive support towards the skin and thereby securing the infusion part (0B).

Figure 27E:
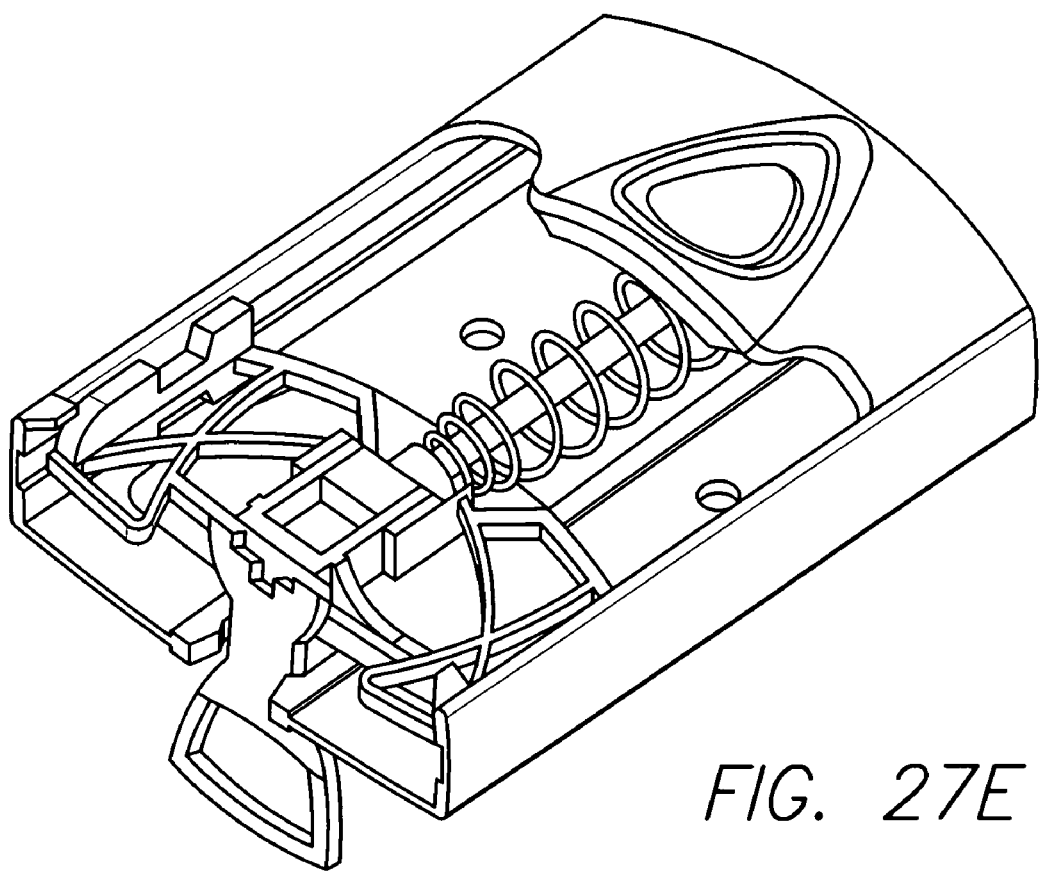
Figure 28E:
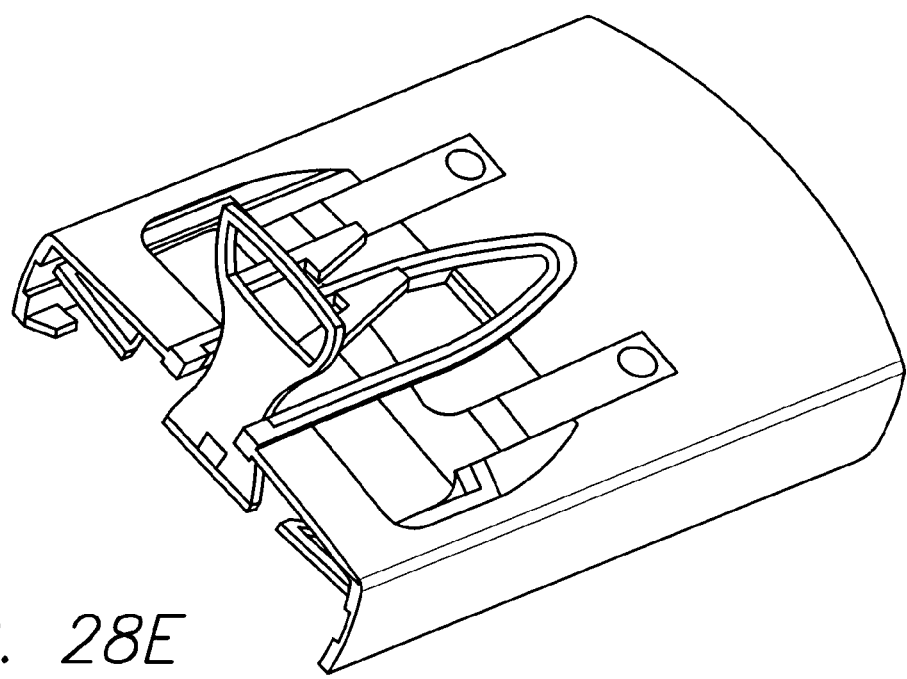

Finally after withdrawal of the insertion needle which in this embodiment is attached to the slidable member (32) in the injector device, it is shown in FIGS. 27E and 28E how the pivoting member (36) is placed in a position where it is embracing the needle thereby protecting the surroundings from getting stung. In order to get into this position the pivoting arm (36) is turned approximately 180° from the position in FIGS. 27D and 28D, and the angle w between the main plane of the injector device and the pivoting arm (36) is approximately 90°.

The invention claimed is:

1. An assembly for the subcutaneous introduction of a cannula of an infusion part into a patient, the assembly comprising:
an infusion part comprising:
an adhesive support;
a base part including at least two retention devices configured to releasably lock a connector to the infusion part, the retention devices extending from an upper surface of a main surface of the base part; and
a cannula extending from the base part and being in fluid connection with a cavity of the infusion part, the cavity being adapted to receive a second cannula extending from the connector and through which a therapeutical substance is administrable; and
an injector device comprising an insertion needle configured to releasably receive the infusion part, the insertion needle extending at least partially through at least a portion of the cannula to insert the cannula into the skin of the patient;
wherein at least a portion of the adhesive support is connected to a portion of the injector device; and a pivoting member connected to the injector device and pivotable from an insertion position into a protection position, the insertion position configured to allow insertion of the needle into the patient and the protection position configured to protect the needle wherein the pivoting member embraces the needle.

2. The assembly of claim 1, wherein the retention devices are positioned at flexible parts of the base part.

3. The assembly of claim 2, wherein the base part comprises at least two flaps on which the retention devices are positioned.

4. The assembly of claim 1, wherein the cannula passes through the adhesive support.

5. The assembly of claim 1, wherein the retention devices each comprise a step.

6. The assembly of claim 1, wherein the retention devices have a triangular shape.

7. The assembly of claim 1, wherein the cannula comprises thermoplastic elastomers (TPE).

8. The assembly of claim 7, wherein the thermoplastic elastomer is selected from the group consisting of polyester ethers, ECDEL, styrene based TPE, olefin based TPE, urethane based TPE, ester based TPE, amid based TPE, polyolefins and silicone rubbers.

9. The assembly of claim 1, wherein the infusion part comprises polypropylene.

10. The assembly of claim 1, wherein a projecting part of a release liner of the adhesive support is fastened to the injector device.

11. The assembly of claim 1, further comprising a release liner of the adhesive support, the release liner comprising at least two separate pieces.

12. The assembly of claim 11, wherein a portion of each piece of the release liner is attached to the injector device during insertion.

13. An assembly for the subcutaneous introduction of a cannula of an infusion part into a patient, the assembly comprising:
an infusion part comprising:
an adhesive support;
a base part including at least two retention devices configured to releasably lock a connector to the infusion part, the retention devices extending from an upper surface of a main surface of the base part; and
a cannula extending from the base part and being in fluid connection with a cavity of the infusion part; and
an injector device comprising:
a housing comprising a longitudinally extending guide;
a slidable member adapted to longitudinally slide relative to the housing;
a needle connected to the slidable member, the needle configured for insertion at least partially through the cannula to insert the cannula into the skin of the patient,
a spring located between a back portion of the housing and the longitudinally slidable member; and
a pivoting member connected to the injector device and pivotable from an insertion position into a protection position, the insertion position configured to allow insertion of the needle into the patient and the protection position configured to protect the needle wherein the pivoting member embraces the needle.

14. The assembly of claim 13, wherein the pivoting member is fastened to the slidable member.

15. The assembly of claim 14, wherein the insertion position of the pivoting member is an insertion angle between about 45° and about 180°, the insertion angle measured in relation to a central axis of the needle.

16. The assembly of claim 14, wherein the insertion position of the pivoting member is an insertion angle between about 80° and about 180°, the insertion angle measured in relation to a central axis of the needle.

17. The assembly of claim 14, wherein the insertion position of the pivoting member is an insertion angle between about 90°, the insertion angle measured in relation to a central axis of the needle.

18. The assembly of claim 13, wherein the pivoting member is placed substantially parallel to the housing when the pivoting member is in the position where the pivoting member embraces the needle.

19. The assembly of claim 13, wherein the pivoting member is placed in an embracing angle with respect to the housing between about 0° and about 180° when the pivoting member is in the position where the pivoting member embraces the needle.

20. The assembly of claim 13, wherein the pivoting member is placed in an embracing angle with respect to the housing between about 90° and about 180° when the pivoting member is in the position where the pivoting member embraces the needle.

21. The assembly of claims 13, wherein the pivoting member can embrace the needle when the slidable member is in a forward position and the spring is in a released state.

22. The assembly of claim 13, wherein the needle is destroyed and secured in the pivoting member in the protection position.

23. The assembly of claim 13, wherein the assembly further comprises locking means for maintaining the pivoting member in the protection position.

24. The assembly of claim 13, the pivoting member has fixing means for releasably fastening a part of the adhesive support to the pivoting member.

25. The assembly of claim 13, wherein a projecting part of a release liner of the adhesive support is unreleasably fastened to the housing.

26. The assembly of claim 13, further comprising a release liner of the adhesive support, the release liner comprising at least two separate pieces.

27. The assembly of claim 26, wherein each piece of the release liner is attached to the pivoting member during insertion and the projecting part of the second piece of the release liner is attached to the housing during insertion.

* * * * *

UNITED STATES PATENT AND TRADEMARK OFFICE
CERTIFICATE OF CORRECTION

PATENT NO. : 7,648,494 B2
APPLICATION NO. : 11/084893
DATED : January 19, 2010
INVENTOR(S) : Kornerup et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 629 days.

Signed and Sealed this

Twenty-third Day of November, 2010

David J. Kappos
*Director of the United States Patent and Trademark Office*